(12) United States Patent
Lu et al.

(10) Patent No.: US 11,291,601 B2
(45) Date of Patent: Apr. 5, 2022

(54) WEARABLE WORKING HEAD FOR NURSING MACHINE

(71) Applicant: SUZHOU ALTON ELECTRICAL & MECHANICAL INDUSTRY CO., LTD., Jiangsu (CN)

(72) Inventors: Weidong Lu, Jiangsu (CN); Qiang Song, Jiangsu (CN); Zhouen Li, Jiangsu (CN); Bo Xiao, Jiangsu (CN); Xianke Zhang, Jiangsu (CN); Xiaoyu Liu, Jiangsu (CN)

(73) Assignee: SUZHOU ALTON ELECTRICAL & MECHANICAL INDUSTRY CO., LTD.

( * ) Notice: Subject to any disclaimer, the term of this patent is extended or adjusted under 35 U.S.C. 154(b) by 60 days.

(21) Appl. No.: 16/765,087

(22) PCT Filed: Aug. 20, 2018

(86) PCT No.: PCT/CN2018/101346
§ 371 (c)(1),
(2) Date: May 18, 2020

(87) PCT Pub. No.: WO2019/095763
PCT Pub. Date: May 23, 2019

(65) Prior Publication Data
US 2022/0008273 A1     Jan. 13, 2022

(51) Int. Cl.
*A61G 9/00* (2006.01)
(52) U.S. Cl.
CPC ............ *A61G 9/006* (2013.01); *A61G 9/003* (2013.01); *A61G 2203/30* (2013.01)

(58) Field of Classification Search
CPC .................. A61G 9/006; A61G 9/003
USPC ........................................ 4/144.2
See application file for complete search history.

(56) References Cited

U.S. PATENT DOCUMENTS

| | | | |
|---|---|---|---|
| 5,342,583 A * | 8/1994 | Son | A61F 5/451 422/107 |
| 5,681,297 A * | 10/1997 | Hashimoto | A61F 5/451 119/164 |
| 6,394,988 B1 | 5/2002 | Hashimoto | |
| 6,443,939 B1 | 9/2002 | Oki et al. | |
| 6,785,916 B2 * | 9/2004 | Tanaka | A61G 9/003 4/450 |

(Continued)

FOREIGN PATENT DOCUMENTS

| | | |
|---|---|---|
| CN | 201399026 | 2/2010 |
| CN | 101933857 | 1/2011 |

(Continued)

OTHER PUBLICATIONS

International Search Report issued in PCT Application No. PCT/CN2018/101346, dated Nov. 1, 2018.

*Primary Examiner* — Huyen D Le
(74) *Attorney, Agent, or Firm* — Barnes & Thornburg LLP; Jeffrey R. Stone

(57) ABSTRACT

A wearable working head for a nursing machine includes a front wearing part, where the front wearing part includes a toilet recess and a urine hood. The urine hood includes a hood wall and a recess enclosed by the hood wall, where the recess is located at an inner side of the hood wall. The hood wall is provided with at least one air vent communicating the recess to the outside of the hood wall.

20 Claims, 18 Drawing Sheets

(56) References Cited

U.S. PATENT DOCUMENTS

| | | | | |
|---|---|---|---|---|
| 10,799,410 B2* | 10/2020 | Lee | ........................ | A61G 9/003 |
| 2017/0020760 A1* | 1/2017 | Sang | ....................... | A61G 9/006 |

FOREIGN PATENT DOCUMENTS

| | | |
|---|---|---|
| CN | 201840402 | 5/2011 |
| CN | 202615575 | 12/2012 |
| CN | 103989563 | 8/2014 |
| CN | 104519846 | 4/2015 |
| CN | 104825266 | 8/2015 |
| CN | 105708605 | 6/2016 |
| CN | 105708607 | 6/2016 |
| CN | 205339269 | 6/2016 |
| CN | 105764453 | 7/2016 |
| CN | 205459551 | 8/2016 |
| CN | 106618910 | 5/2017 |
| CN | 106726086 | 5/2017 |
| CN | 106726087 | 5/2017 |
| CN | 106991797 | 7/2017 |
| CN | 107205874 | 9/2017 |
| CN | 107320231 | 11/2017 |
| EP | 3 064 179 A1 | 9/2016 |
| JP | 4288158 | 10/1992 |
| JP | 2008048912 | 12/2010 |
| WO | 2014/208814 | 12/2014 |

\* cited by examiner

WEARABLE WORKING HEAD FOR NURSING MACHINE

CROSS-REFERENCE TO RELATED APPLICATIONS

This application is a U.S. National Stage Application of co-pending International Patent Application No. PCT/CN2018/101346 filed on Aug. 20, 2018 which claims the priority of China Patent Application Nos. 201721556814.9, 201711157945.4, 201711158139.9, 201711158836.4, and 201721556917.5, which are filed on Nov. 20, 2017 with China National Intellectual Property Administration, the disclosures of all of which are hereby incorporated herein by reference in their entireties.

TECHNICAL FIELD

This application relates to the field of medical machinery, and for example, to a wearable working head of a nursing machine.

BACKGROUND

With the improvement of people's living standards, bedridden patients who are unable to take care of themselves with respect to urination and defecation due to e.g. cardiovascular and cerebrovascular diseases are increasing year by year, which brings great pressure on families and society. Because the patients cannot take care of themselves with defecation, they need the assistance of accompanying staff. The uncertainty of a patient's defecation times increases the workload of the accompanying staff, and also causes great pain and burden to the patient's physiology, especially his/her mental state. Therefore, medical institutions and patients' families often use a dedicated toilet nursing machine to automatically clean human excreta and also clean and dry the patients' lower bodies by a nursing machine main unit and a wearable working head. A urine hood of the working head is used for urination purposes of the human body.

Because the air in the urine hood cannot be effectively replenished, during suction there is not sufficient airflow formed in the urine hood to suck away the urine and the flushing water in the urine hood. As such, the suction of the urine hood cannot be performed thoroughly resulting in poor cleaning effects.

SUMMARY

The present application provides a wearable working head for a nursing machine, which has a superior suction effect on the urine hood.

The present application provides a wearable working head for a nursing machine, the wearable working head comprises a front wearing part which is provided with a toilet recess and a urine hood, wherein the urine hood comprises a hood wall and a recess enclosed by the hood wall, and wherein recess is located inside the hood wall, and the hood wall is provided with at least one air vent communicating the recess to the outside of the hood wall.

In one embodiment, the at least one air vent is provided in the hood wall, and wherein the at least one air vent is provided in the number of two and the two air vents are disposed to be spaced apart along a left-right orientation, or the at least one air vent is provided in plurality and the plurality of air vents are arranged one behind another.

In one embodiment, the urine hood is provided with a hood opening, and the recess is recessed from the hood opening of the urine hood; the urine hood is provided with an annular folded edge that surrounds the hood opening of the urine hood and that is connected to the hood wall, wherein the annular folded edge is annularly arranged at an edge of the hood wall and surrounds the hood opening of the urine hood; and the front wearing part is further provided with a cushion washer connected to the annular folded edge, the cushion washer forming a frame of the urine hood that is configured for attaching to the human body.

In one embodiment, the front wearing part further comprises a tray and an elastic connector, wherein the tray is configured to directly or indirectly support buttocks of the human body, and the elastic connector is configured to connect the urine hood to the tray, and wherein the toilet recess is defined in the tray.

In one embodiment, the front wearing part further comprises a tray configured to directly or indirectly support buttocks of the human body, wherein the tray is provided with the toilet recess configured to receive an excreta; the tray is provided with a front edge portion disposed in front of the toilet recess, the front edge portion defining a concave area corresponding to a tailbone of the human body.

In one embodiment, the concave area extends forward to a foremost end of the tray.

In one embodiment, the tray comprises a first housing, and the toilet recess is defined in the first housing; the front edge portion is a part of the first housing, the first housing comprising a bottom wall and a front wall extending upward from a front edge of the bottom wall, wherein the front wall is integrally connected to the front edge portion and blocks on a rear side of the concave area.

In one embodiment, the concave area is covered with a cushion, and the cushion further covers the front wall.

In one embodiment, a recess between the concave area and the toilet recess is defined above the front wall, the concave area is covered with a cushion, and the cushion covers the recess.

In one embodiment, the part of the cushion covering the concave area is thicker than the part of the cushion covering the recess.

In one embodiment, the tray is further provided with a left front nozzle and a right front nozzle configured for spraying water towards an inside of the toilet recess, wherein the left front nozzle is disposed at a left rear side of the concave area, and the right front nozzle is disposed at a right rear side of the concave area.

In one embodiment, the tray is further provided with a first water inlet connector, a first connection water pipe having two ends, a second connection water pipe having two ends, and a third connection pipe having three ends; wherein the first connection water pipe connects a first end of the third connection pipe to the left front nozzle, the second connection water pipe connects a second end of the third connection pipe to the right front nozzle, and a third end of the third connection water pipe is connected to the first water inlet connector.

In one embodiment, the tray comprises a first housing and the toilet recess is defined in the first housing, the front edge portion is a part of the first housing, the left front nozzle and the right front nozzle are each fixed to the first housing, the first housing comprises a left front mounting through slot disposed on a left front side of the toilet recess and a right front mounting through slot disposed on a right front side of the toilet recess, wherein the left front nozzle is mounted in the left front mounting through slot, and the right front nozzle is mounted in the right front mounting through slot.

In one embodiment, each of the left front nozzle and the right front nozzle comprises a first nozzle part and a second nozzle part, the first nozzle part is integrally provided with a second water inlet connector, the first nozzle part and the second nozzle part enclose a nozzle water cavity configured such as to allow water to be sprayed out via a water outlet defined in the first nozzle part after entering the nozzle water cavity via the second water inlet connector.

In one embodiment, each of the left front nozzle and the right front nozzle is fixed to the first housing, and wherein the left front nozzle and the left front mounting through slot are sealed together by gluing, and the right front nozzle and the right front mounting through slot are sealed together by gluing.

In one embodiment, the left front nozzle is provided with at least one water outlet facing the toilet recess and configured to spray water toward the right rear side, and the right front nozzle is provided with at least one water outlet facing the toilet recess and configured to spray water toward the left rear side.

In one embodiment, the front wearing part is provided with an air supplement port.

In one embodiment, the front wearing part is further provided with an excreta inlet and a drying and blowing hole that communicate with the toilet recess, and wherein the air supplement port is located at a side lower part of the drying and blowing hole and at a side upper part of the excreta inlet.

In one embodiment, the wearable working head further comprises a rear part and an air supplement pipeline assembled together with the front wearing part, wherein when the air pressure in the toilet recess is a negative air pressure relative to the outside of the working head, the working head is configured to allow air in the outside of the working head to successively pass through an inner cavity of the rear part and the air supplement pipeline to be supplied to the toilet recess.

In one embodiment, the wearable working head further comprises a rear part and an air supplement pipeline assembled together with the front wearing part, wherein an inner cavity of the rear part is in communication with the outside of the working head; the air supplement pipeline comprises a first end and a second end that are opposite to each other, the air supplement port forms a first end port of the air supplement pipeline, and a second end port of the air supplement pipeline is in a direct communication with the inner cavity of the rear part; the working head is configured to allow air in the inner cavity of the rear part to enter the air supplement pipeline via the second end port and further be supplied to the toilet recess via the air supplement port.

In one embodiment, the air supplement pipeline further comprises an outer bending section disposed outside the rear part, and wherein two opposite ends of the outer bending section are each connected to the rear part.

In one embodiment, the outer bending section comprises a left bending section and a right bending section that are joined together.

In one embodiment, the rear part comprises a front side wall and a rear end wall that are opposite to each other in front and back orientation, a left side wall and a right side wall that are opposite to each other in left and right orientation; the front side wall, the rear end wall, the left side wall, and the right side wall surround the inner cavity; the front side wall faces the front wearing part, and the rear end wall comprises a rear end wall left part and a rear end wall right part; the left bending section is connected to the rear end wall left part, and the right bending section is connected to the rear end wall right part, the rear end wall left part and the rear end wall right part are joined together in left and right orientation, and the left bending section and the right bending section are joined together in left and right orientation.

In one embodiment, the front wearing part comprises a first housing and the toilet recess is defined in the first housing, the air supplement pipeline comprises a first pipe section integrally connected to the first housing, a second pipe section integrally connected to the front side wall, and a third pipe section integrally connected to the left bending section; wherein the first pipe section is joined with the second pipe section, the second pipe section is joined with the third pipe section, the second pipe section and the third pipe section are disposed in the inner cavity of the rear part, and the first pipe section passes backwards through the front side wall to enter the inner cavity of the rear part.

In one embodiment, the wearable working head further comprises a rear part and a locking structure configured for locking the front wearing part to the rear part; the locking structure comprises a first locking member arranged on the front wearing part, a second locking member arranged on the rear part, a third locking member arranged on the front wearing part, and a fourth locking member arranged on the rear part; the first locking member and the second locking member are locked together, and the third locking member and the fourth locking member are locked together; the second locking member is operative to move towards the fourth locking member under the action of an external force to be unlocked with the first locking member, and the fourth locking member is operative to move towards the second locking member under an external force to be unlocked with the third locking member.

In one embodiment, the second locking member is operative to perform a translating motion towards the fourth locking member under a driving action of the external force to be unlocked with the first locking member, and the fourth locking member is operative to perform a translating motion towards the second locking member under a driving action of the external force to be unlocked with the third locking member.

In one embodiment, the rear part is further arranged with a left side wall, a right side wall opposite to the left side wall, a first through via penetrating the left side wall, and a second through via penetrating the right side wall; the second locking member comprises a first action part operative to move along the first through via toward the fourth locking member under the driving action of the external force thus driving the second locking member to move towards the fourth locking member, and the fourth locking member comprises a second action part operative to move along the second through via toward the second locking member under the driving action of the external force thus driving the fourth locking member to move towards the second locking member.

In one embodiment, the first action part comprises a first outer plate operative to be directly driven by an external force, a first side plate, and a first folded edge; an outer end of the first side plate is connected to the first outer plate; the first folded edge is bent and extends from an inner end of the first side plate; the first through via comprises a first inner port and first outer port respectively located at an inner end and an outer end of the first through via, and the first folded edge blocks at an edge of the first inner port.

In one embodiment, the rear part is provided with an inner cavity, a front side wall, and a left side wall and a right side wall that are opposite to each other; the front side wall, the left side wall, and the right side wall each surround at a side of the inner cavity, and the front side wall faces the front wearing part, and the first locking member passes backwards through the front side wall to enter the inner cavity of the rear part; the front side wall is fixedly connected with a first blocking member disposed in the inner cavity; the rear part is further provided with a first restoring spring, wherein a first end of the first restoring spring is blocked by the first blocking member and a second end of the first restoring spring opposite to the first end is blocked by the second locking member.

In one embodiment, the first blocking member is provided with a first sleeve, the second locking member is provided with a second sleeve nested with the first sleeve, and wherein the first end of the first restoring spring is received in the first sleeve, and the opposite second end of the first restoring spring is received in the second sleeve.

In one embodiment, the second locking member is provided with a first hook locked with the first locking member, the first blocking member is provided with a first connecting part integrally connected between the first sleeve and the front side wall, and the first connecting part and the first locking member are respectively disposed on a left side and a right side of the first hook.

In one embodiment, the first connecting part defines a first retreating space configured for receiving the first hook.

In one embodiment, the wearable working head further comprises a urine detection circuit, the urine detection circuit comprising a first group of urine sensors and a second group of urine sensors, wherein the first group of urine sensors comprises at least two first urine sensors spaced apart from each other, and the second group of urine sensors comprises at least two second urine sensors spaced apart from each other; wherein in response to at least two first urine sensors outputting a liquid detected signal signaling that a liquid is detected or at least two second urine sensors outputting the liquid detected signal, the urine detection circuit is configured to output a urine signal, and in response to only one first urine sensor outputting the liquid detected signal, or only one second urine sensor outputting the liquid detected signal, or only one first urine sensor and only one second urine sensor each outputting the liquid detected signal, the urine detection circuit is configured to not output the urine signal.

In one embodiment, there are provided two of the first urine sensors and two of the second urine sensors, and the urine detection circuit comprises a first detection circuit, a second detection circuit, and a urine signaling circuit; wherein the two first urine sensors belong to the first detection circuit, the two second urine sensors belong to the second detection circuit; wherein the first detection circuit is configured to output a high level in response to both of the two first urine sensors each outputting the liquid detected signal, and is further configured to output a low level in response to neither of the two first urine sensors outputting the liquid detected signal or only one of two first urine sensors outputting the liquid detected signal; wherein the second detection circuit is configured to output a high level in response to both of the two second urine sensors each outputting the liquid detected signal, and is further configured to output a low level in response to neither of the two second urine sensors outputting the liquid detected signal or only one of the two second urine sensors outputting the liquid detected signal; and wherein the urine signaling circuit is configured to output the urine signal in response to receiving the high level output by the first detection circuit or by the second detection circuit, and is further configured to not output the urine signal in response to receiving the low level output by both of the first detection circuit and the second detection circuit.

In one embodiment, the urine detection circuit comprises a first detection circuit, a second detection circuit, and a urine signaling circuit, wherein the first urine sensors belong to the first detection circuit, wherein the first detection circuit comprises a first metal oxide semiconductor (MOS) tube, all the first urine sensors are connected in parallel to a same electrode of the first MOS tube; wherein the second urine sensors belong to the second detection circuit, the second detection circuit comprises a second MOS tube, all the second urine sensors are connected in parallel to a same electrode of the second MOS tube; and wherein the urine signaling circuit comprises a third MOS tube, and the first detection circuit and the second detection circuit are connected in parallel to a same electrode of the third MOS tube.

The present application further provides a wearable working head for a nursing machine, the wearable working head comprising a front wearing part, the front wearing part comprising a tray configured to directly or indirectly support buttocks of a human body; the tray comprises a first housing, and the first housing of the tray is formed with a toilet recess configured to receive an excreta; the first housing is provided with a front edge portion disposed in front of the toilet recess, and the front edge portion defines a concave area corresponding to a tailbone of the human body; the first housing comprises a front wall disposed at a front side of the toilet recess and a rear wall disposed at a rear side of the toilet recess, wherein the front wall is located between the concave area and the toilet recess, and the concave area is covered with a cushion.

In one embodiment, a recess between the concave area and the toilet recess is defined above the front wall, and the cushion covers the recess, and wherein the part of the cushion covering the concave area is thicker than the part of the cushion covering the recess.

In one embodiment, the tray is further provided with a left front nozzle and a right front nozzle configured for spraying water towards an inside of the toilet recess, wherein the left front nozzle is disposed at a left rear side of the concave area, and the right front nozzle is disposed at a right rear side of the concave area; wherein the first housing further comprises a left front mounting through slot located on a left front side of the toilet recess and a right front mounting through slot located on a right front side of the toilet recess, wherein the left front nozzle is mounted in the left front mounting through slot, and the right front nozzle is mounted in the right front mounting through slot.

The present application further provides a wearable working head for a nursing machine, the wearable working head comprising a front wearing part, a rear part, and an air supplement pipeline, wherein the front wearing part is configured for being worn by the human body, the rear part is configured to be assembled together with the front wearing part, wherein the front wearing part is provided with an air supplement port, an inner cavity of the rear part is in communication with the outside of the wearable working head; the air supplement pipeline comprises a first end and a second end that are opposite to each other, the air supplement port forms a first end port of the air supplement pipeline, and a second end port of the air supplement pipeline is in a direct communication with the inner cavity of the rear part, and wherein air in the inner cavity of the rear part is allowed to enter the air supplement pipeline via the second end port and further be supplied to the toilet recess via the air supplement port.

In one embodiment, the air supplement pipeline comprises an outer bending section disposed outside the rear part, and two opposite ends of the outer bending section are each connected to the rear part.

In one embodiment, the outer bending section comprises a left bending section and a right bending section that are joined together; the rear part includes a front side wall and a rear end wall that are opposite to each other in front and back orientation, a left side wall and a right side wall that are opposite to each other in left and right orientation; the front side wall, the rear end wall, the left side wall, and the right side wall surround the inner cavity; the front side wall faces the front wearing part, and the rear end wall comprises a rear end wall left part and a rear end wall right part; the left bending section is connected to the rear end wall left part, and the right bending section is connected to the rear end wall right part, wherein the rear end wall left part and the rear end wall right part are joined together in left and right orientation, and the left bending section and the right bending section are joined together in left and right orientation.

In one embodiment, the front wearing part includes a first housing, and the toilet recess is defined in the first housing, the air supplement pipeline includes a first pipe section integrally connected to the first housing, a second pipe section integrally connected to the front side wall, and a third pipe section integrally connected to the left bending section; the first pipe section is joined with the second pipe section, the second pipe section is joined with the third pipe section, where the second pipe section and the third pipe section are disposed in the inner cavity of the rear part, and the first pipe section passes backwards through the front side wall to enter the inner cavity of the rear part.

The present application further provides a wearable working head for a nursing machine, the wearable working head comprising a front wearing part, a rear part, and a locking structure configured for locking the front wearing part to the rear part; the locking structure comprises a first locking member arranged on the front wearing part, a second locking member arranged on the rear part, a third locking member arranged on the front wearing part, and a fourth locking member arranged on the rear part, wherein the first locking member and the second locking member are locked together, the third locking member and the fourth locking member are locked together; and the second locking member is operative to move towards the fourth locking member under the action of an external force to be unlocked with the first locking member, and the fourth locking member is operative to move towards the second locking member under an external force to be unlocked with the third locking member.

In one embodiment, the rear part is further provided with a left side wall, a right side wall opposite to the left side wall, a first through via penetrating the left side wall, and a second through via penetrating the right side wall; the second locking member comprises a first action part operative to move along the first through via toward the fourth locking member under the driving action of an external force thus driving the second locking member to move towards the fourth locking member; the fourth locking member comprises a second action part operative to move along the second through via toward the second locking member under the driving action of an external force thus driving the fourth locking member to move towards the second locking member.

In one embodiment, the first action part comprises a first outer plate operative to be directly driven by an external force, a first side plate, and a first folded edge; an outer end of the first side plate is connected to the first outer plate; the first folded edge is bent and extends from an inner end of the first side plate; the first through via includes a first inner port and first outer port respectively located at an inner end and an outer end of the first through via; and the first folded edge blocks at an edge of the first inner port to prevent the first action part from separating outwards from the first through via.

In one embodiment, the rear part is provided with an inner cavity, a front side wall, and a left side wall and a right side wall that are opposite to each other; the front side wall, the left side wall, and the right side wall each surround at a side of the inner cavity; the front side wall faces the front wearing part, and the first locking member passes backwards through the front side wall to enter the inner cavity of the rear part; the front side wall is fixedly connected with a first blocking member disposed in the inner cavity; the rear part is further provided with a first restoring spring, wherein a first end of the first restoring spring is blocked by the first blocking member and a second end of the first restoring spring opposite to the first end is blocked by the second locking member; the first blocking member is provided with a first sleeve, and the second locking member is provided with a second sleeve nested with the first sleeve, wherein the first end of the first restoring spring is received in the first sleeve, and the opposite second end of the first restoring spring is received in the second sleeve.

DETAILED DESCRIPTION

Technical solutions according to the embodiments of the present application will be described and illustrated below with reference to the drawings of the embodiments of the present application.

The inventor found that multiple urine sensors are usually arranged in a working head, and a liquid detected signal, that a liquid is detected, output by any one urine sensor will mistakenly trigger a urine disposing program, such that even when a small amount of water or other liquid left or condensed in the working head moves to or lands in a detectable range of one of the urine sensors, the urine disposing program will be mistakenly triggered.

Referring to FIGS. 1 to 21, the wearable working head for a nursing machine provided by the embodiments of the present application is suitable for being worn on the crotch of a human body for long periods of time to serve purposes of automatically cleaning urine and defecation of the human body, thereby reducing the burden on family members and care staff. The wearable working head is connected to a nursing machine main unit (not shown in the figures) through a pipeline, which may include a sewage hose, a water inlet pipe, a data transmission line, and so on. A suction device of the nursing machine main unit sucks an excreta collected by the wearable working head into the nursing machine main unit via the pipeline. The wearable working head may include a front wearing part, a rear part, a gel cushion 90, and a locking structure. The front wearing part is used for wearing on the human body. The locking structure is used for locking the front wearing part and the rear part together.

Figure 1:
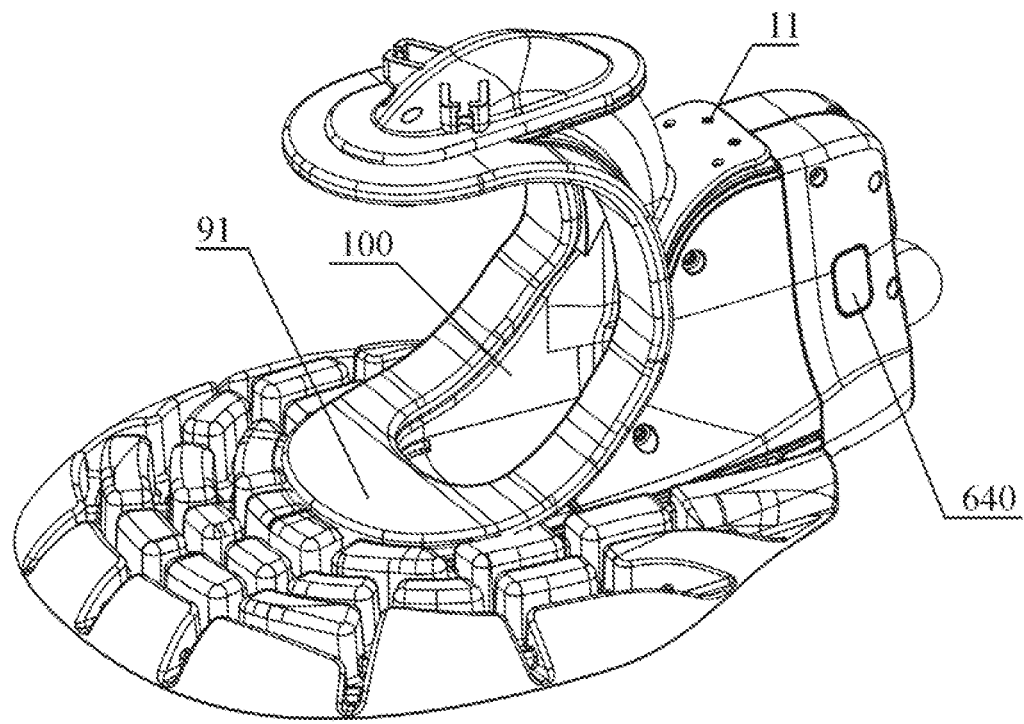
FIG. 1 is a perspective view of a wearable working head for a nursing machine according to an embodiment of the present disclosure.
Figure 2:
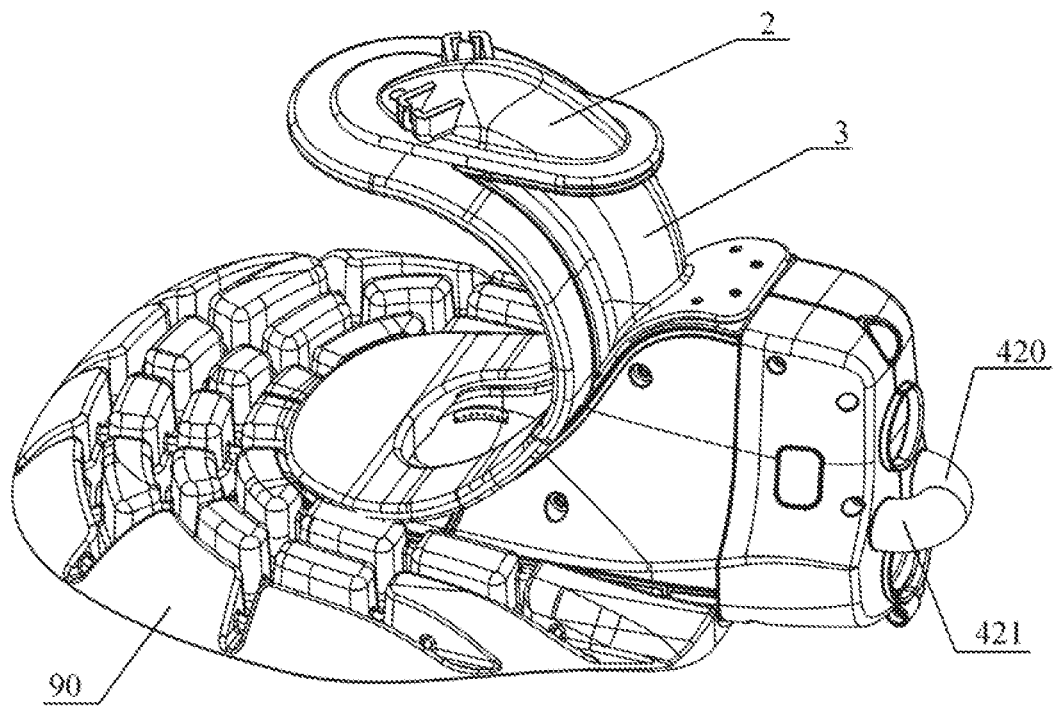
FIG. 2 is perspective view of a wearable working head for a nursing machine viewed from another angle according to an embodiment of the present disclosure.
Figure 3:
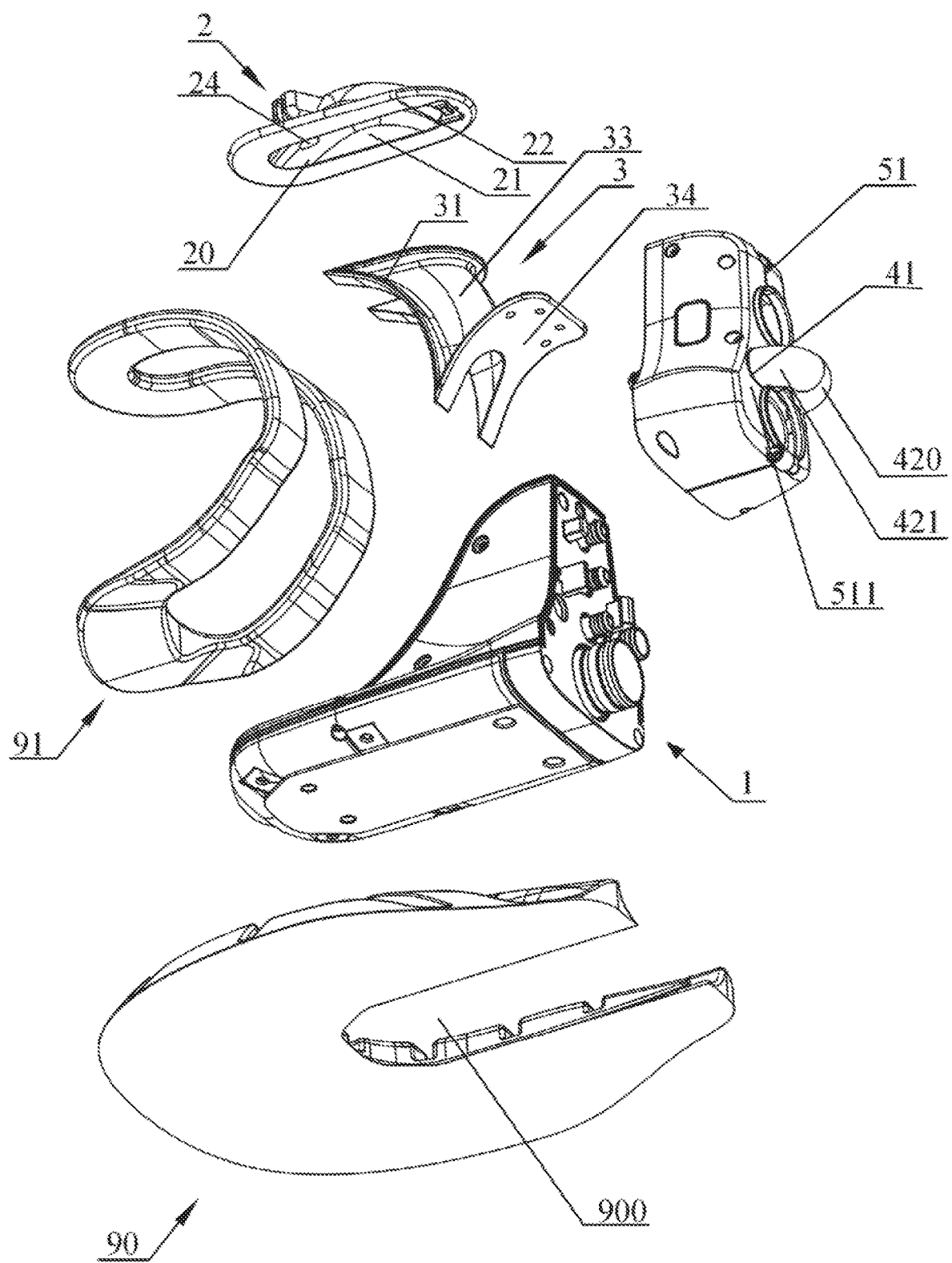
FIG. 3 is an exploded view of a wearable working head for a nursing machine according to an embodiment of the present disclosure.

Referring to FIGS. 1 to 3, the front wearing part may include a tray 1, a urine hood 2, an elastic connector 3 and a gel washer 91. The tray 1 defines a toilet recess 10, which is configured for receiving an excreta. The gel washer 91 forms a frame of the toilet recess 10 for attaching to a human body and a frame of the urine hood 2 for attaching to the human body. The gel is a soft material with a good shape recovery and it is suitable for curling, so that compared with a buffer washer made of other materials, the gel washer 91 may better buffer an pressure between the working head and the human body, it can prevent the working head from causing an excessive pressure to the human body, and improve comfort of the human body after the working head is worn. Meanwhile, the gel washer 91 can better adapt to and conform to the human body thereby preventing the human excreta from leaking. The working head is used for being worn on the human body to dispose the excreta of the human body. A part of the gel washer 91 extends along a periphery of a slot rim 100 of the toilet recess 10, and another part of the gel washer 91 extends along a periphery of a hood opening 20 of the urine hood 2. The gel washer 91 is bent into a U-shape located between the urine hood 2 and the toilet recess 10, which has an elongated ring shape in a flat state after being unfolded. The gel washer 91 has a surface covered with a TPU protective film to prevent gel from overflow. The protective film is made of thermoplastic polyurethane elastomer (TPU), which may be transparent or opaque. One characteristic of the gel is that it is easy to be broken resulting in leakage, while the TPU protective film may significantly prevent the gel from being broken leading to leakage.

The tray 1 may be configured to directly or indirectly support buttocks of the human body. The toilet recess 10 is defined in the tray 1. The elastic connector 3 connects the urine hood 2 to the tray 1. The tray 1, the elastic connector 3 and the urine hood 2 are connected together to form a U-shape. The elastic connector 3 is disposed at a rear side of the gel washer 91, and a left side and a right side of the elastic connector 3 are each connected to the gel washer 91. The left side and right side of the elastic connector 3 are each tightly attached to the gel washer 91. The elastic connector 3 may be made of rubber and has a milky white color. The elastic connector 3 may be provided with a left folded edge 30 and a right folded edge 31, the left folded edge 30 and the right folded edge 31 are disposed at the left side and right side of the elastic connector 3, and the left folded edge 30 and the right folded edge 31 are each located at the rear side of the gel washer 91 and are connected to the gel washer 91. The left folded edge 30 and the right folded edge 31 are each hermetically connected to the gel washer 91. The left folded edge 30 and the right folded edge 31 are each bonded to the gel washer 91. The urine hood 2 may be provided with a recess 21 recessed from the hood opening 20 for urination purposes. The elastic connector 3 may be provided with a guide slot 32 for communicating the recess 21 with the toilet recess 10. The recess 21 and the guide slot 32 may be smoothly joined together. An inner surface of the recess 21 may smoothly be joined with an inner surface of the guide slot 32. The inner surface of the recess 21 and the inner surface of the guide slot 32 may be aligned at the joint. The guide slot 32 may have a curved cross section.

Figure 4:
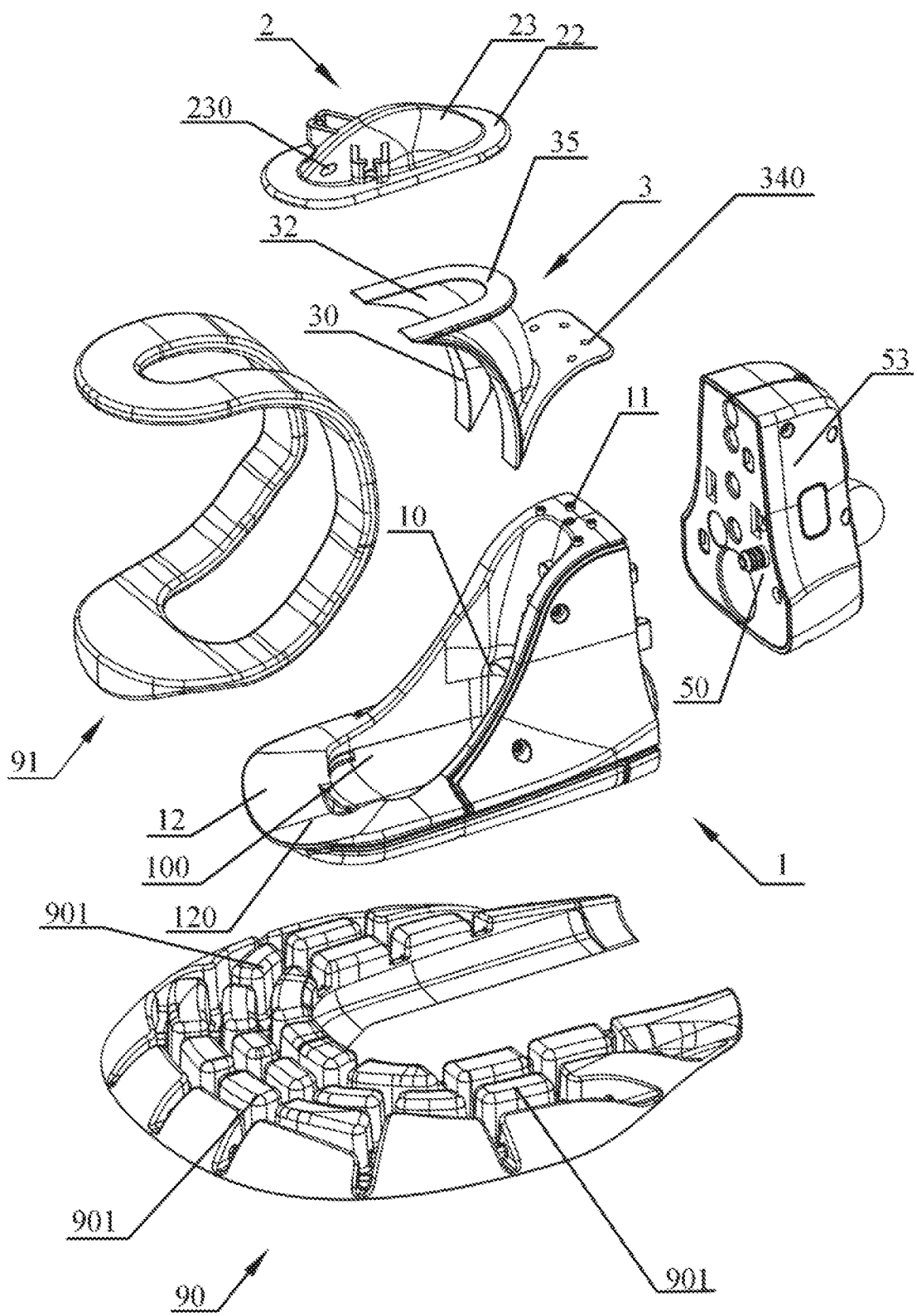
FIG. 4 is an exploded view of a wearable working head for a nursing machine viewed from another angle according to an embodiment of the present disclosure.

Referring to FIGS. 3 and 4, the elastic connector 3 may further include a main body 33. The left folded edge 30 may be bent leftward from a front left edge of the main body 33, the right folded edge 31 may be bent rightward from a front right edge of the main body 33, and the guide slot 32 may be arranged in the main body 33. The main body 33 may have a curved cross section. The elastic connector 3 may further include a rear side connector 34 bent backward from a lower edge of the main body 33 and an upper folded edge 35 bent and extended from an upper edge of the main body 33, and the rear side connector 34 may be connected to an upper end of the tray 1. The rear connector 34 may be adhered to an upper end surface of the tray 1, the rear connector 34 may be provided with at least one positioning hole 340, the upper end of the tray 1 may be provided with at least one positioning protrusion 11 corresponding to the at least one positioning hole 340, and a positioning protrusion 11 may pass through a corresponding positioning hole 340. In this solution, a matching between the at least one positioning hole 340 and the at least one positioning protrusion 11 is used for defining an accurate installation position of the elastic connector 3 relative to the tray 1, and the elastic connector 3 is bonded to the tray 1 after it is arranged at the accurate installation position. The elastic connector 3 may further include the upper folded edge 35 connected to the urine hood 2.

The urine hood 2 may be provided with an annular folded edge 22 surrounding the hood opening 20 of the urine hood 2, and the upper folded edge 35 is connected to a rear lower surface of the annular folded edge 22. The recess 21 of the urine hood 2 has relatively smooth left and right sides, so that urine on the left side or the right side of the recess 21 is relatively easy to flow away and be sucked away after the human body lies on the left or right side wearing the working head, thus the urine hood 2 is not vulnerable to liquid retention even when the human body lies on a side. The gel washer 91 may be bonded to a lower surface of the annular folded edge 22. The gel cushion 90 may be provided with a notch 900 for placing the tray 1. The gel cushion 90 may include a right side part located on a right side of the tray 1, a left side part located on a left side of the tray 1, a front side part located on a front side of the tray 1, and multiple humps 901 distributed on an upper surface of the left side part, an upper surface of the right side part, and an upper surface of the front side part. The working head may further include a cushion cover (not shown in the FIGs) sleeved on periphery of the gel cushion 90, a position of the cushion cover corresponding to the notch 900 is connected to a bottom of the tray 1, and the position of the cushion cover corresponding to the notch 900 is connected to the bottom of the tray 1 through a hook and loop and a magnetic buckle for a magnetic attachment. The gel cushion 90 may also be integrated with the gel washer 91 to form a whole gel cushion. The upper end of the left folded edge 30 is connected to the left front end of the upper folded edge 35, and the upper end of the right folded edge 31 is connected to the right front end of the upper folded edge 35. The upper folded edge 35 may be bonded to the urine hood 2, and the upper folded edge 35 may have a curved shape. Each of the left folded edge 30 and the right folded edge 31 may have a curved shape.

Figure 8:
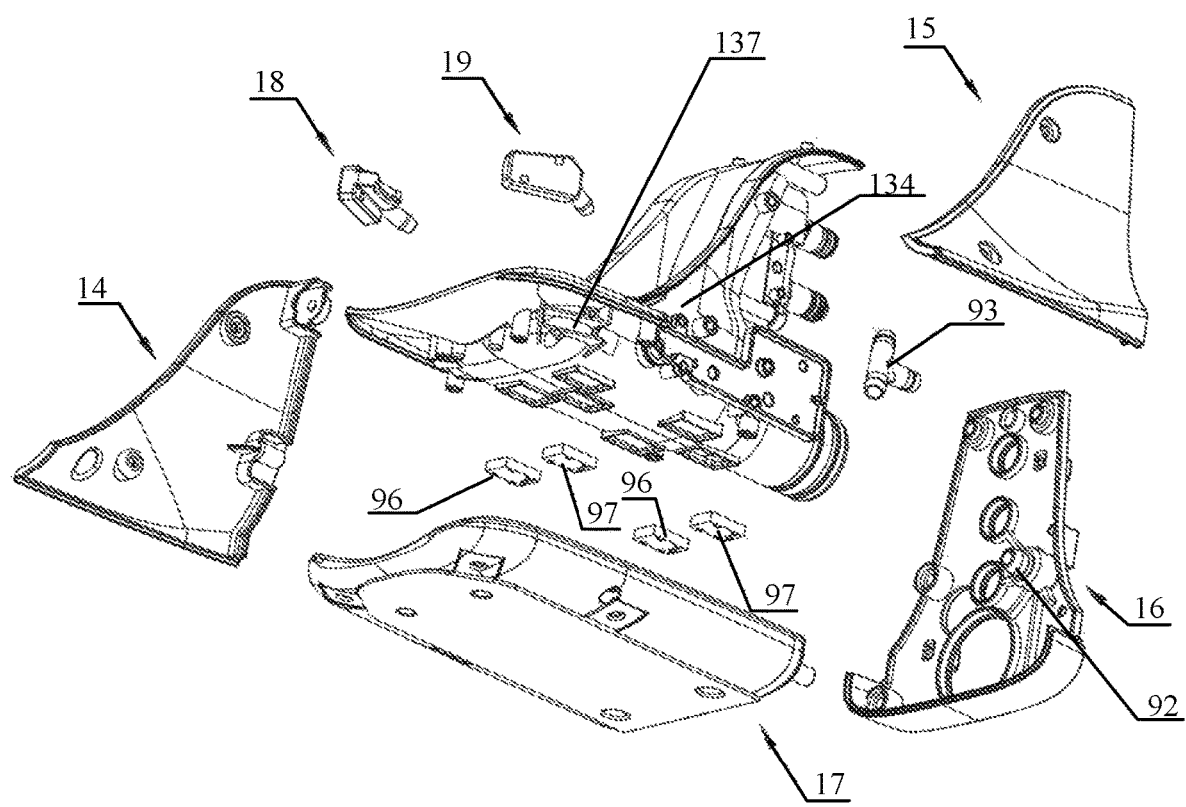
FIG. 8 is an exploded view of a tray of a wearable working head for a nursing machine according to an embodiment of the present disclosure.
Figure 14:
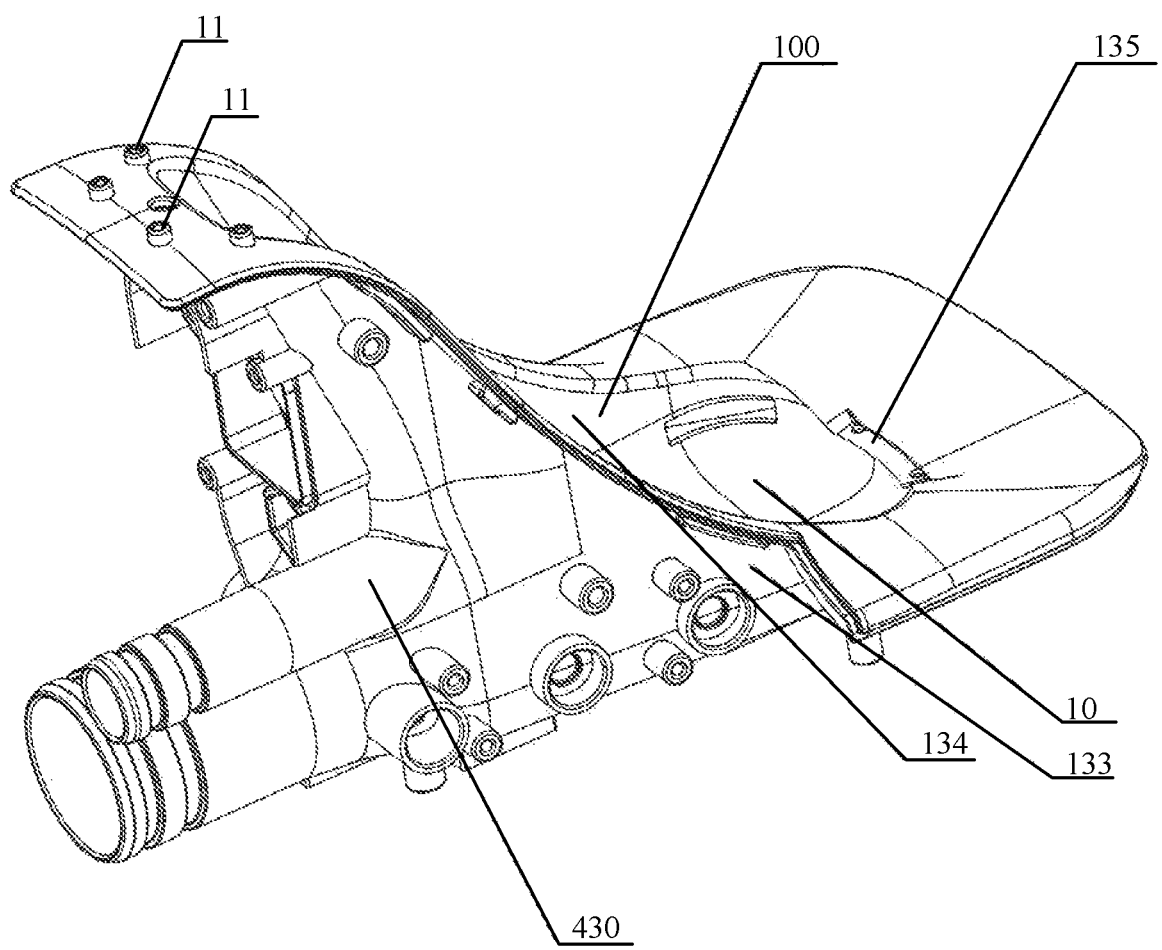
FIG. 14 is a perspective view of a first housing and a first pipe section of a wearable working head for a nursing machine viewed from another angle according to an embodiment.
Figure 15:
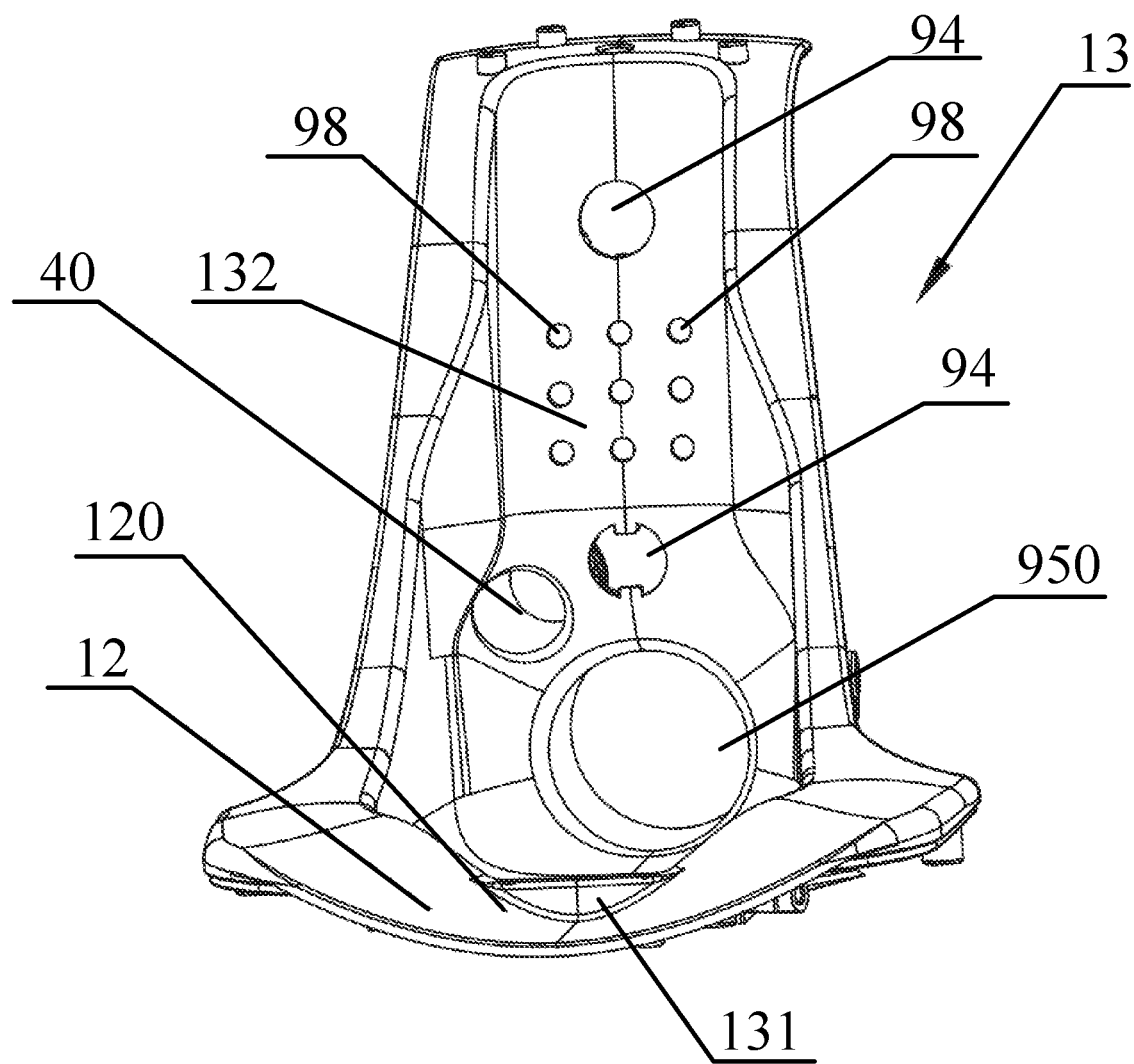
FIG. 15 is a perspective view of a first housing of a wearable working head for a nursing machine according to an embodiment of the present disclosure.
Figure 16:
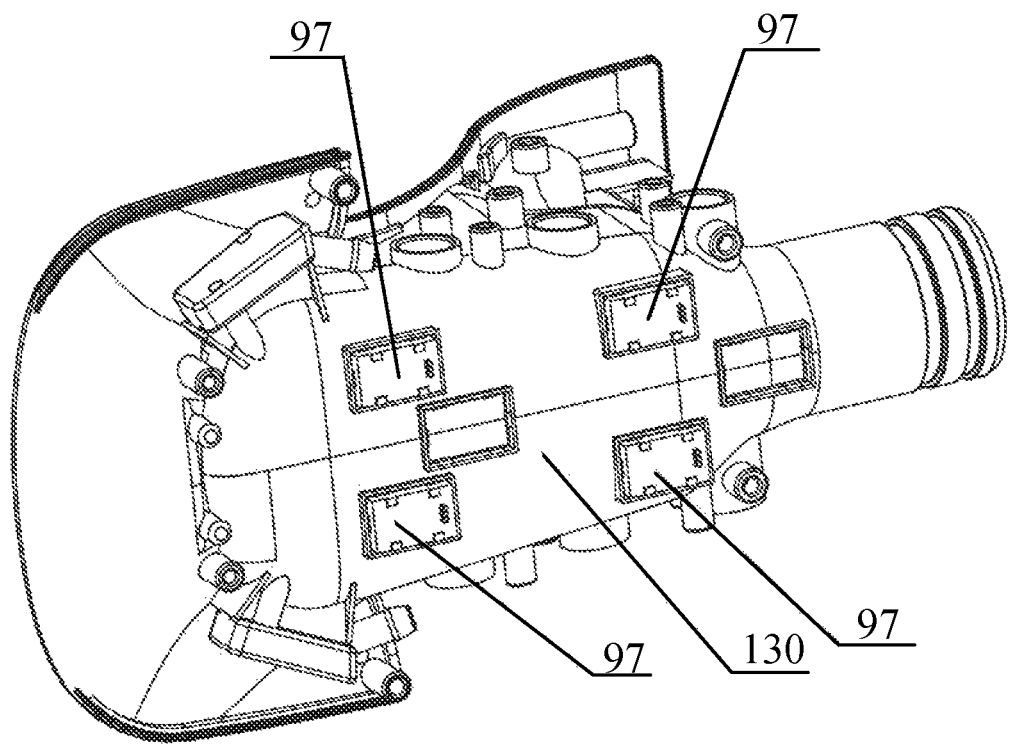
FIG. 16 is a perspective view of a first housing etc. of a wearable working head for a nursing machine according to an embodiment of the present disclosure (where each urine sensor, left and right front nozzles are assembled with the first housing).
Figure 17:
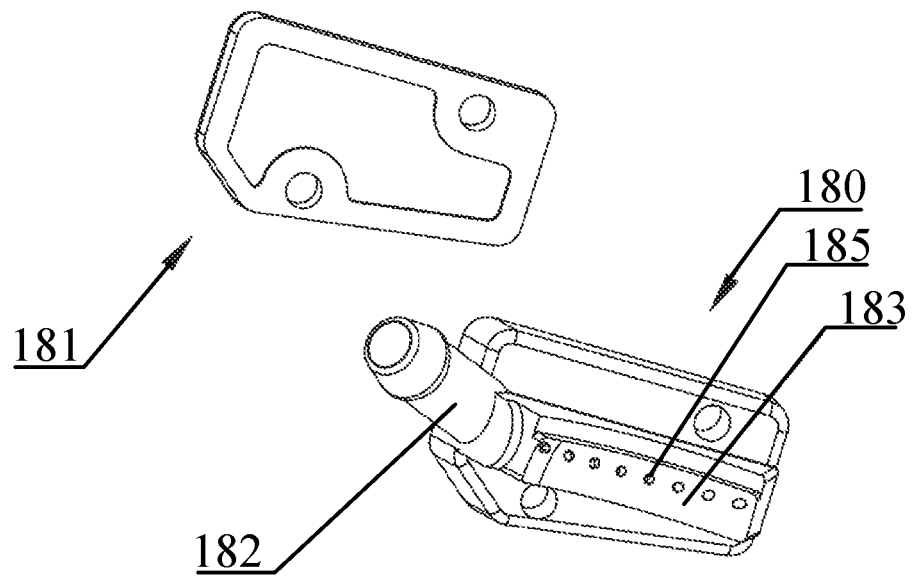
FIG. 17 is an exploded view of a right front nozzle of a wearable working head for a nursing machine according to an embodiment of the present disclosure.
Figure 18:
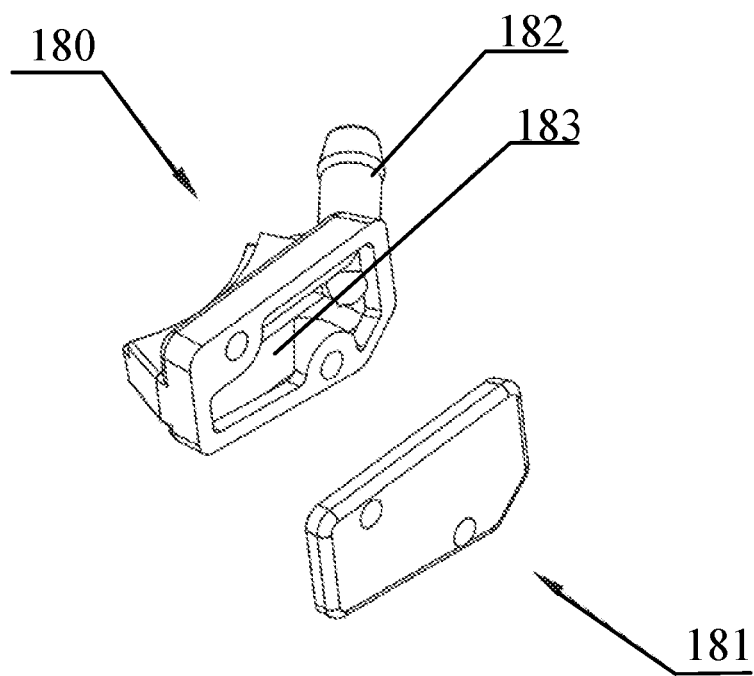
FIG. 18 is an exploded view of a right front nozzle of a wearable working head for a nursing machine viewed from another angle according to an embodiment of the present disclosure.
Figure 19:
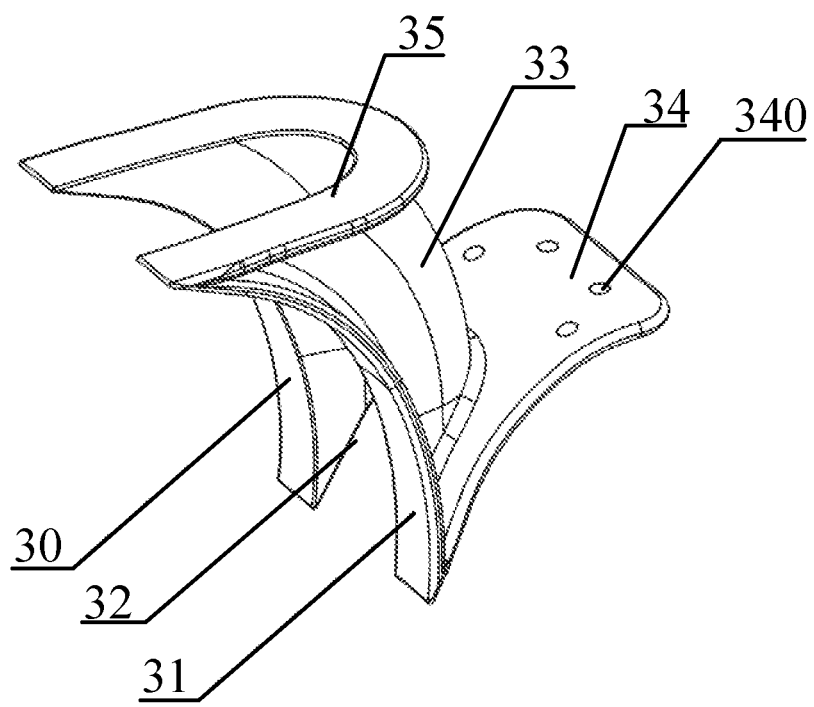
FIG. 19 is a perspective view of an elastic connector of a wearable working head for a nursing machine according to an embodiment of the present disclosure.

The tray 1 may further be provided with a front edge portion 12 located at front of the toilet recess 10. The front edge portion 12 defines a concave area 120 corresponding to a tailbone of the human body, and the concave area 120 is covered with a cushion (in this embodiment, the cushion may be a gel washer 91, and the cushion may also be a gel pad, a silicone pad, a sponge pad, an airbag pad, and etc., where in this embodiment, the gel washer 91 covers the concave area 120). The front edge portion 12 of the related art will cause a greater pressure on the tailbone of the human body, resulting in discomfort at the tailbone after the working head is worn. In this solution, the concave area 120 is provided, and a cushion is covered on this concave area 120, after the working head is worn, a pressure at the tailbone of the human body is directly or indirectly carried by the concave area 120, thus it can greatly reduce the discomfort at the tailbone, improve wearing comfort of the human body, and ensure comfort of the tailbone after long-term wearing. The concave area 120 and the cushion covered on the concave area 120 directly or indirectly support the tailbone of the human body to improve the wearing comfort of the human body. The concave area 120 extends forward to a foremost end of the tray 1. Referring to FIG. 8, the tray 1 may include a first housing 13, a first side wall 14, a second side wall 15, a rear side wall 16, and a bottom side wall 17. The toilet recess 10 is defined in the first housing 13, the front edge portion 12 is a part of the first housing 13, and a material of the first housing 13 may be doped with Nano-silver particles to achieve antibacterial and bactericidal effects and reduce a undesirable odors of the toilet recess. The first housing 13, the first side wall 14, the second side wall 15, the rear side wall 16 and the bottom side wall 17 are assembled together, and joints between them may be sealed by gluing. The first housing 13 may include a bottom wall 130, a front wall 131 extending upward from a front edge portion of the bottom wall 130, a rear wall 132 located at a rear side of the toilet recess 10 and extending upward, a left wall 133 extending upward from a left edge of the bottom wall 130, and a right wall 134 extending upward from a right edge of the bottom wall 130, the front wall 131 is integrally connected to the front edge portion 12 and blocked at the rear side of the concave area 120. The cushion further covers the front wall 131. The cushion is bonded to a top end of the front wall 131. Referring to FIG. 14, a recess 135 located between the concave area 120 and the toilet recess 10 may be formed above the front wall 131. The cushion covers the recess 135. A part of the cushion covering the concave region 120 may be thicker than a part of the cushion covering the recess 135. The cushion may be bonded to the surface of the concave area 120. The front wall 131 may be integrally connected to the front edge portion 12 and blocked at the rear side of the concave area 120. The left wall 133, the right wall 134, the bottom wall 130, the front wall 131 and the rear wall 132 are each a wall of the toilet recess 10. The front wall 131 has a height slightly lower than that of other walls of the toilet recess 10. In this embodiment, the gel washer 91 may cover the front wall 131, and the gel washer 91 may be bonded to the top end of the front wall 131.

The tray 1 may further be provided with a left front nozzle 18 and a right front nozzle 19, which are configured for spraying water towards an inside of the toilet recess 10. The left front nozzle 18 is located on a left front side of the toilet recess 10 and the right front nozzle 19 is located on a right front side of the toilet recess 10. According to this design, compared with a single front nozzle, the left front nozzle 18 and the right front nozzle 19 can provide more balanced and sufficient flushing and discharging on an excreta in the toilet recess 10, and better flushing and discharging effect on left and right edge positions of the toilet recess 10. The left front nozzle 18 may be disposed at the left rear side of the concave area 120, and the right front nozzle 19 may be disposed at the right rear side of the concave area 120. In the related art, a front nozzle is usually arranged in the middle of the front edge portion 12, such that the front edge portion 12 with a large height in the middle and the height may not be effectively reduced, the concave area 120 is provided in this solution and the front nozzle is replaced by the left front nozzle 18 and the right front nozzle 19, so that the concave area 120 may be arranged in a suitable area near the left front nozzle 18 and the right front nozzle 19, which can greatly reduce the discomfort to the tailbone. The left front nozzle 18 and the right front nozzle 19 are each fixed to the first housing 13. The left front nozzle 18 is located on the left front side of the toilet recess 10, and the right front nozzle 19 is located on the right front side of the toilet recess 10.

The first housing 13 may include a left front mounting through slot 136 located at the left front side of the toilet recess 10 and a right front mounting through slot 137 located at the right front side of the toilet recess 10. The left front nozzle 18 is mounted in the left front mounting through slot 136 and the right front nozzle 19 is mounted in the right front mounting through slot 137. Each of the left front nozzle 18 and the right front nozzle 19 may include a one-piece first nozzle part 180 and a one-piece second nozzle part 181. The first nozzle part 180 is integrally provided with a second water inlet connector 182. The first nozzle part 180 and the second nozzle part 181 enclose a nozzle water cavity 183. Each of the left front nozzle 18 and the right front nozzle 19 may be fixed to the first housing 13 by screws, and the left front nozzle 18 and the left front mounting through slot 136 may be sealed together by gluing. The right front nozzle 19 and the right front mounting through slot 137 may be sealed together by gluing. The left front nozzle 18 may be provided with multiple water outlets 184 facing the toilet recess 10 and spraying water toward the right rear side, the right front nozzle 19 may be provided with multiple water outlets 185 facing the toilet recess 10 and spraying water toward the left rear side, and water may enter the nozzle water cavity 183 via a second water inlet connector 182 and then be sprayed out through the water outlets 184 and 185 formed in the first nozzle part 180.

Referring to FIG. 8, the tray 1 may further be provided with a first water inlet connector 92, a first connection water pipe (not shown) having two ends, a second connection water pipe (not shown) having two ends, and a third connection pipe 93 having three ends. The first connection water pipe connects one end of the third connection pipe 93 to the left front nozzle 18. The second connection water pipe connects another end of the third connection pipe 93 to the right front nozzle 19, and a third end of the third connection water pipe connects to the first water inlet connector 92. The first water inlet connector 92, the first connection water pipe having both ends, the second connection water pipe having two ends, and the third connecting pipe 93 having three ends are located inside the tray 1. The first connection water pipe and the second connection water pipe may be hosepipes with connection heads, and the third connecting pipe 93 may have a T-shape or Y-shape. When the third end of the third connection water pipe 93 is not long enough, it may be connected to the first water inlet connector 92 via a water pipe.

Figure 5:
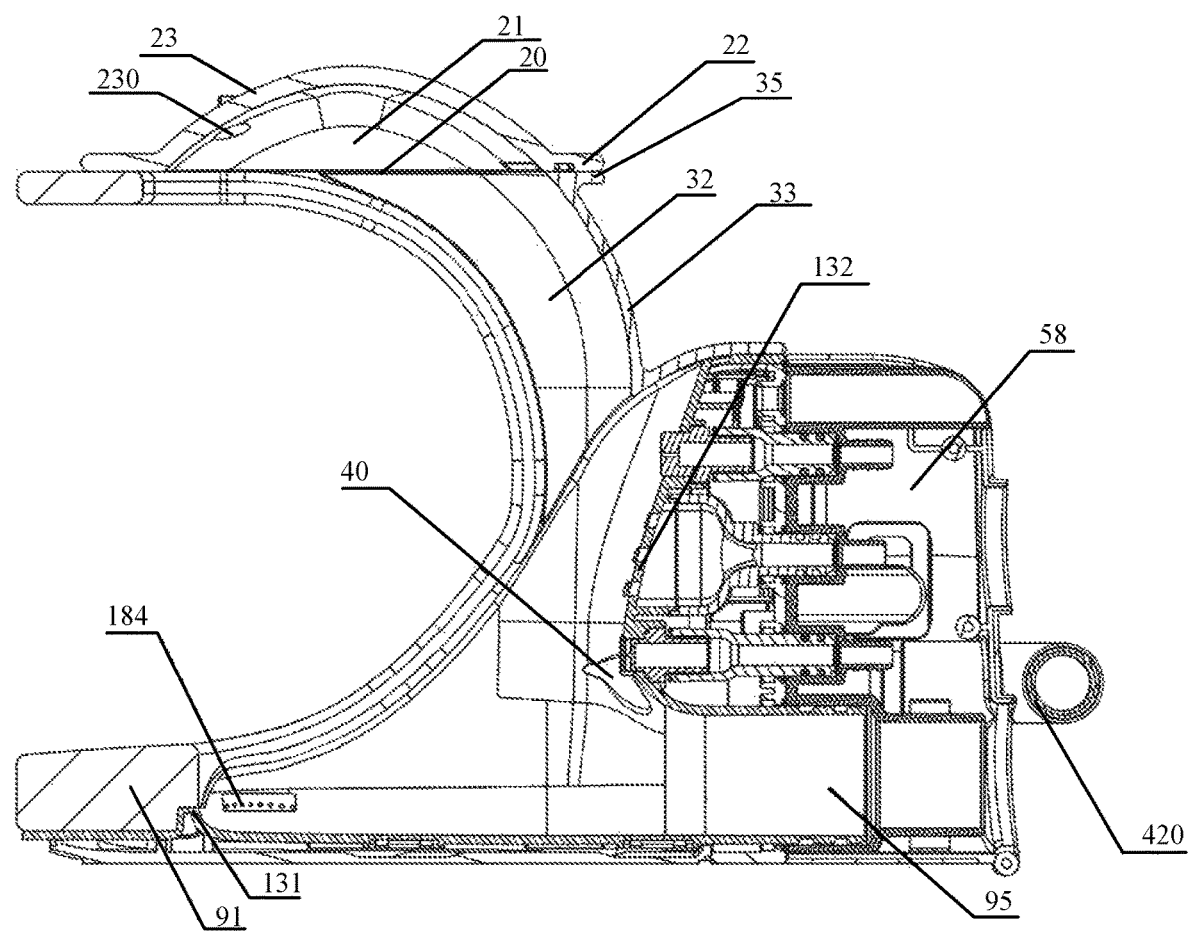
FIG. 5 is a vertical cross-sectional view of a wearable working head for a nursing machine according to an embodiment of the present disclosure.
Figure 6:
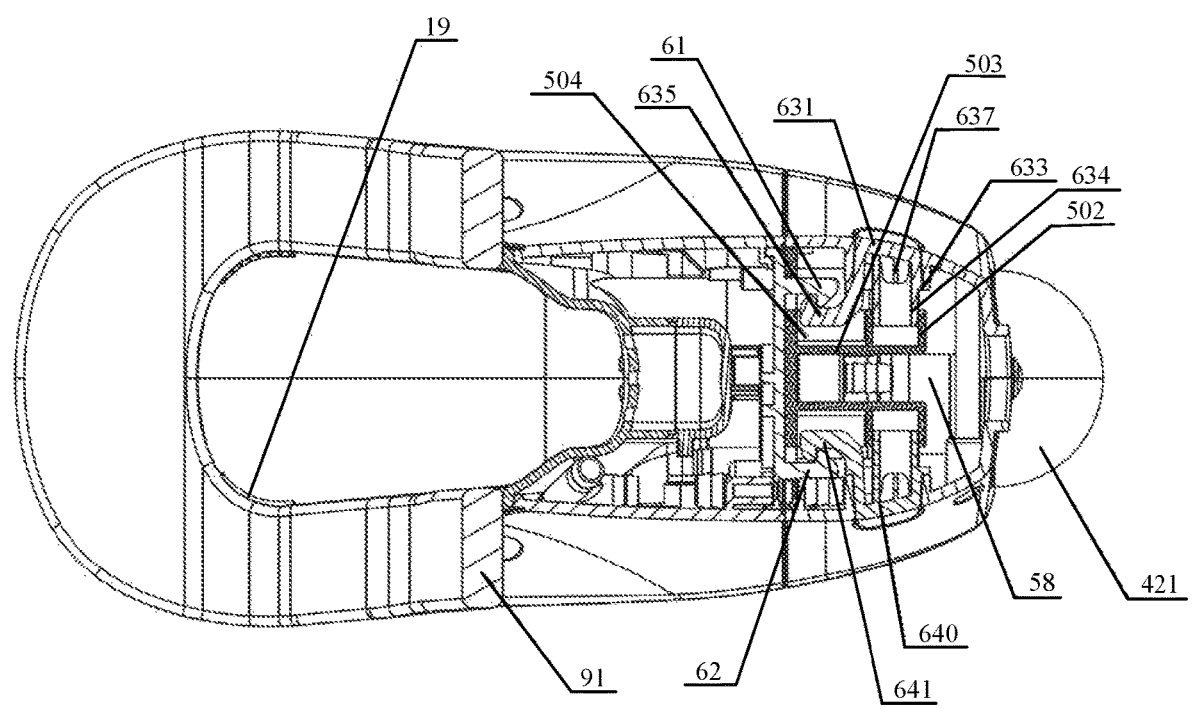
FIG. 6 is a horizontal cross-sectional view of a wearable working head for a nursing machine according to an embodiment of the present disclosure (the cross-section cuts through a locking structure).
Figure 7:
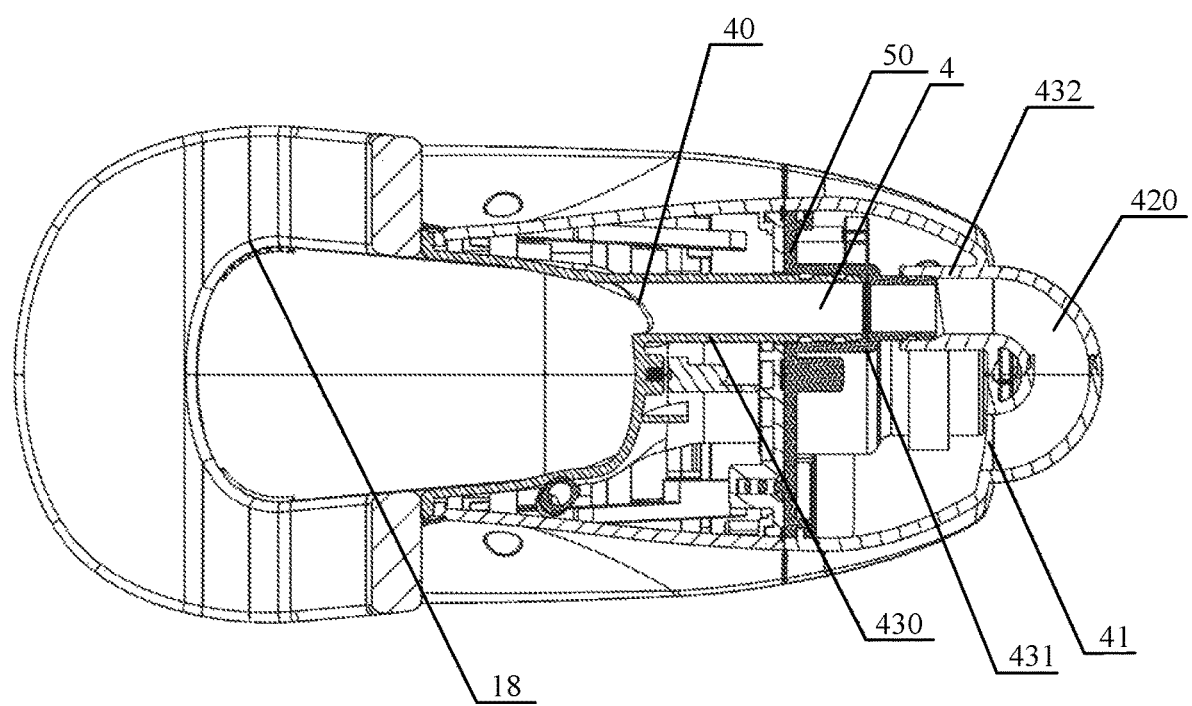
FIG. 7 is another horizontal cross-sectional view of a wearable working head for a nursing machine according to an embodiment of the present disclosure (the cross-section cuts through an air supplement pipeline).

Referring to FIGS. 4 and 5, the urine hood 2 may be provided with a hood wall 23 protruding outward, so that the hood wall 23 encloses the recess 21. The recess 21 is disposed inside the hood wall 23, and the hood wall 23 may be provided with at least one air vent 230 communicating the recess 21 to outside of the hood wall 23. According to this design, when the nursing machine performs a sucking operation, the recess 21 will have a negative air pressure relative to the outside of the hood wall 23, and air in the outside of hood wall 23 may be replenished into the recess 21 via the air vent 230, so that there is relatively sufficient air in the recess 21, and further sufficient suction air flow may be formed inside the urine hood 2, so that urine and flushing water in the recess 21 can be sufficiently sucked and cleaned, providing a good suction effect on the urine hood 2. The recess 21 is disposed opposite to the toilet recess 10. The air vent 230 may be arranged at a front part of the hood wall 23. There may be provided two air vents 230 spaced apart and one behind the other or multiple air vents 230 arranged one behind another. The recess 21 is recessed from the hood opening 20 of the urine hood 2, the annular folded edge 22 may be annularly arranged at the edge of the hood wall 23 and surrounds the hood opening 20. The gel washer 91 is a type of cushion washer, the gel washer 91 forms a cushion washer connected to the annular folded edge 22, and the cushion washer forms a frame of the urine hood 2 for attaching to the human body.

An inner surface of the hood wall 23 may be provided with a first conductive line (not shown in the FIGs) and a second conductive line (not shown in the FIGs) that are exposed and spaced apart from each other. After a urination is performed by the human body, the first conductive line and the second conductive line would be electrically communicated by urine. The first conductive line attached to the inner surface of the urine hood 2 may be implemented as a conductive silicone, an aluminum foil, a metal plating layer or a metal wire, and the second conductive line attached to the inner surface of the urine hood 2 may be implemented as a conductive silicone, an aluminum foil, a metal plating, or a metal wire. The first conductive line and the second conductive line may be spaced from each other by at least one air vent 230. The first conductive line and the second conductive line may each surround the air vent 230. The first conductive line and the second conductive line may each be a non-closed loop.

Referring to FIGS. 3 to 12, the rear part may include a front side wall 50 and a rear end wall 51 that are opposite to each other, a left side wall 52 and a right side wall 53 that are opposite to each other. The front side wall 50, the rear end wall 51, the left side wall 52 and the right side wall 53 surround an inner cavity 58. The front side wall 50 faces the front wearing part. The rear end wall 51 includes a rear end wall left part 510 and a rear end wall right part 511. The rear part includes a left shell 54 and a right shell 55. The rear end wall left part 510 and the left side wall 52 belong to a part of the left shell 54, and the rear end wall right part 511 and the right side wall 53 belong to a part of the right shell 55. The left shell 54, the right shell 55 and the front side wall 50 enclose the inner cavity 58. The left shell 54, the right shell 55 and the front side wall 50 are snap-fitted to a clamping slot 57 through an arranged locking strip 56. The rear end wall left part 510 and the rear end wall right part 511 are joined together in left and right orientation.

Referring to FIGS. 7 to 15, the front wearing part may be provided with multiple drying and blowing holes 98, a rear water spraying port 94, and an air supplement port 40 for supplying air into the toilet recess 10. According to this design, when the nursing machine performs a suction operation, the air supplement port 40 may supply air into the toilet recess 10, which can ensure sufficient suction air flow of the inside of the toilet recess 10 and promote sufficient suction of excreta, flushing water and so on in the toilet recess 10, so that the good suction effect on the excreta in the toilet recess 10 can be achieved. The drying and blowing holes 98, the rear water spraying port 94 and the air supplement port 40 are arranged on the rear wall 132 of the toilet recess 10.

The working head may further include an air supplement pipeline 4. The inner cavity 58 of the rear part is communicated with outside of the working head, which is not closed, so that the outside and the inner cavity 58 of the rear part may normally exchange air, joint positions of the left shell 54, the right shell 55 and the front side wall 50 are not sealed, which facilitates ventilation of the inner cavity 58 with the outside. The air supplement pipeline 4 has a first end and a second end that are opposite to each other. The air supplement port 40 forms a first end port of the air supplement pipeline 4, a second end port 41 of the air supplement pipeline 4 is directly communicated with the inner cavity 58 of the rear part, and air in the inner cavity 58 may enter the air supplement pipeline 4 from the second end port 41 and be replenished into the toilet recess 10 via the air supplement port 40. The air supplement pipeline 4 may have a length greater than 10 cm and a circular cross section with a diameter in a range of 12 mm to 14 mm.

Air outside the working head may be sucked in between the front wearing part and the human body through the air supplement pipeline 4, and the air is sucked out along with an excreta through a drain pipe. When the air pressure in the toilet recess 10 is a negative pressure with respect to the outside of the working head, the air outside the working head is supplied into the toilet recess 10 through the inner cavity 58 of the rear part and the air supplement pipeline 4 in sequence. The second end port 41 of the air supplement pipeline 4 may be located within the inner cavity 58 of the rear part. The air supplement pipeline 4 may be bent in the inner cavity 58 of the rear part, so it can prevent the excreta and cleaned water from leaking through the air supplement pipeline 4. Even if a small amount of the excreta or cleaning water may enter the air supplement pipeline 4, once the suction operation starts, the excreta or cleaning water would be able to be sucked out of the air supplement pipeline 4 through the air supplement port 40 and further out of the working head as long as there is no leakage. A part of the air supplement pipeline 4 may be bent upward in the inner cavity 58 of the rear part, or a part of the air supplement pipeline 4 may be bent leftward or rightward in the inner cavity 58 of the rear part. The air supplement pipeline 4 may include an outer bending section located outside the rear part, and two opposite ends of the outer bending section are each connected to the rear part. The outer bending section may have a shape of a hollow bent pipe. The outer bending section may include a left bending section 420 and a right bending section 421 that are joined together. The second end port 41 may be opened at the rear end wall right part 511 and forms an end port of the right bending section 421, the left bending section 420 may be connected to the rear end wall left part 510, the right bending section 421 may be connected to the rear end wall right part 511 and the left bending section 420 and the right bending section 421 are joined together in left and right orientation. The joint connection of the left bending section 420 and the right bending section 421 may be sealed. The right bending section 421 may be integrally connected to the rear end wall right part 511, and the left bending section 420 may be integrally connected with the rear end wall left part 510.

The air supplement pipeline 4 may include a first pipe section 430 integrally connected to the first housing 13, a second pipe section 431 integrally connected to the front side wall 50, and a third pipe section 432 integrally connected to the left bending section 420. The first pipe section 430 is joined with the second pipe section 431, the second pipe section 431 is joined with the third pipe section 432, the second pipe section 431 and the third pipe section 432 are arranged in the inner cavity 58 of the rear part, and the first pipe section 430 passes backwards through the front side wall 50 to enter the inner cavity 58 of the rear part.

It can also be designed that the second end port 41 of the air supplement pipeline 4 is directly communicated with the outside of the working head, and when the air pressure in the toilet recess 10 is a negative pressure with respect to the outside (when the nursing machine performs a sucking operation, the air pressure in the toilet recess 10 is a negative pressure relative to the outside), the air outside the working head may enter the air supplement pipeline 4 from the second end port 41 and be replenished into the toilet recess 10 through the air supplement port 40. The air supplement pipeline 4 may pass through the front wearing part to enter the rear part and then pass through the rear part, or the air supplement pipeline 4 may pass through the front wearing part to enter the rear part, and the second end port 41 of the air supplement pipeline 4 is opened in the shell of the rear part. The suction pipeline 95 communicating with the toilet recess 10 passes through the rear part, the excreta inlet 950 of the suction pipeline 95 is arranged at the rear wall 132, the excreta inlet 950 communicates with the toilet recess 10, the air supplement port 40 is located at a side lower part of the drying and blowing hole 98, and the air supplement port 40 is located at a side upper part of the excreta inlet 950.

Figure 9:
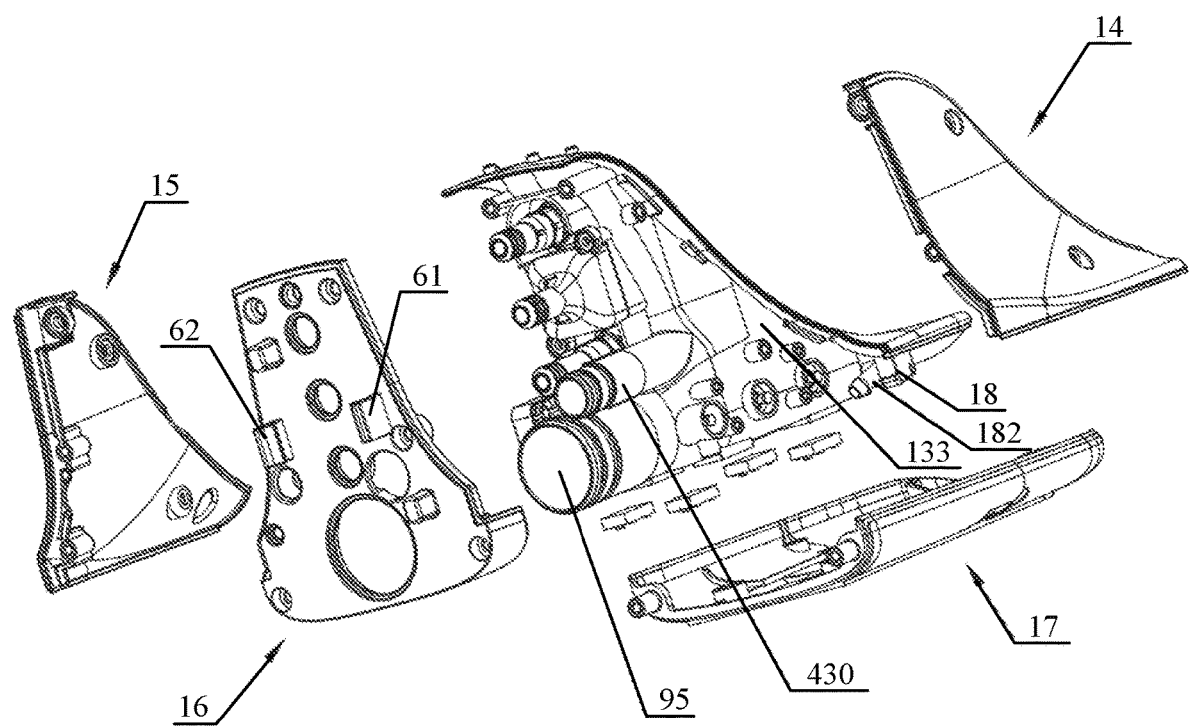
FIG. 9 is an exploded view of a tray of a wearable working head for a nursing machine viewed from another angle according to an embodiment of the present disclosure.
Figure 10:
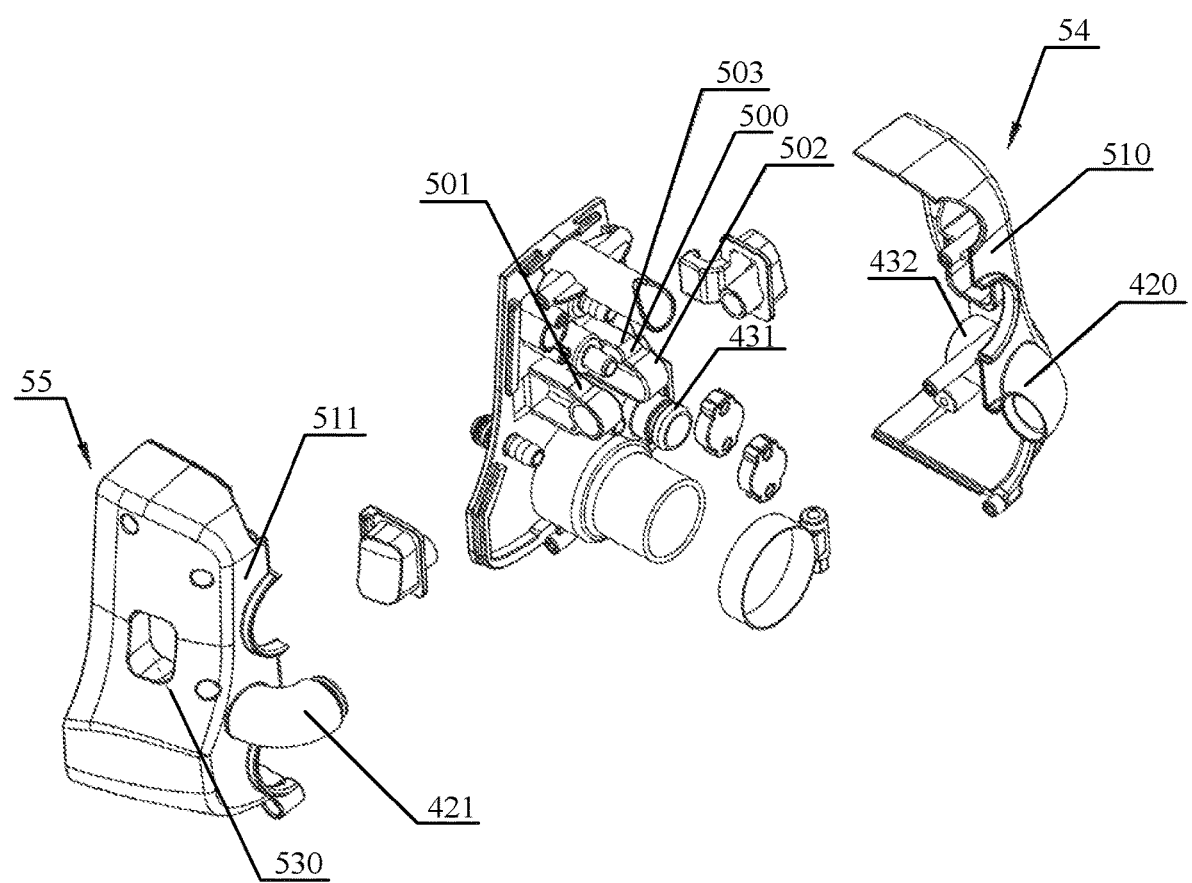
FIG. 10 is an exploded view of a rear part of a wearable working head for a nursing machine according to an embodiment of the present disclosure.
Figure 20:
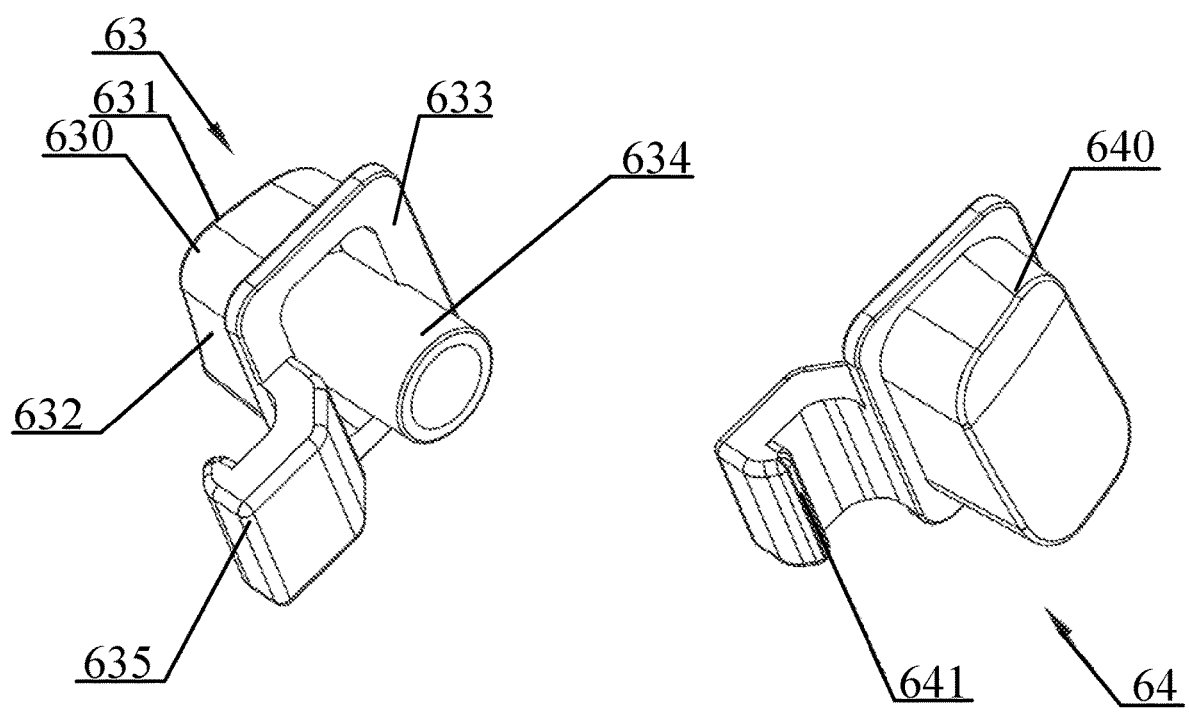
FIG. 20 is a perspective view of a second locking member and a fourth locking member of a wearable working head for a nursing machine according to an embodiment of the present disclosure.

Referring to FIGS. 9 and 20, the locking structure may include a first locking member 61 and a third locking member 62 arranged on the front wearing part, a second locking member 63 and a fourth locking member 64 arranged on the rear part, where the first locking member 61 and the second locking member 63 are locked together. The second locking member 63 may be operative to move towards the first locking member 61 under the action of an external force to be unlocked with the first locking member 61. The third locking member 62 and the fourth locking member 64 are locked together, the second locking member 63 may be operative to move towards the fourth locking member 64 under an external force to be unlocked with the first locking member 61, the fourth locking member 64 may be operative to move towards the second locking member 63 under an external force to be unlocked with the third locking member 62. The first locking member 61 and the third locking member 62 are symmetrical in left and right orientation, and the second locking member 63 and the fourth locking member 64 are symmetrical in left and right orientation. The second locking member 63 may be operative to perform a translating motion towards the fourth locking member 64 under a driving action of the external force to be unlocked with the first locking member 61, and the fourth locking member 64 may be operative to perform a translating motion towards the second locking member 63 under a driving action of the external force to be unlocked with the third locking member 62.

Figure 11:
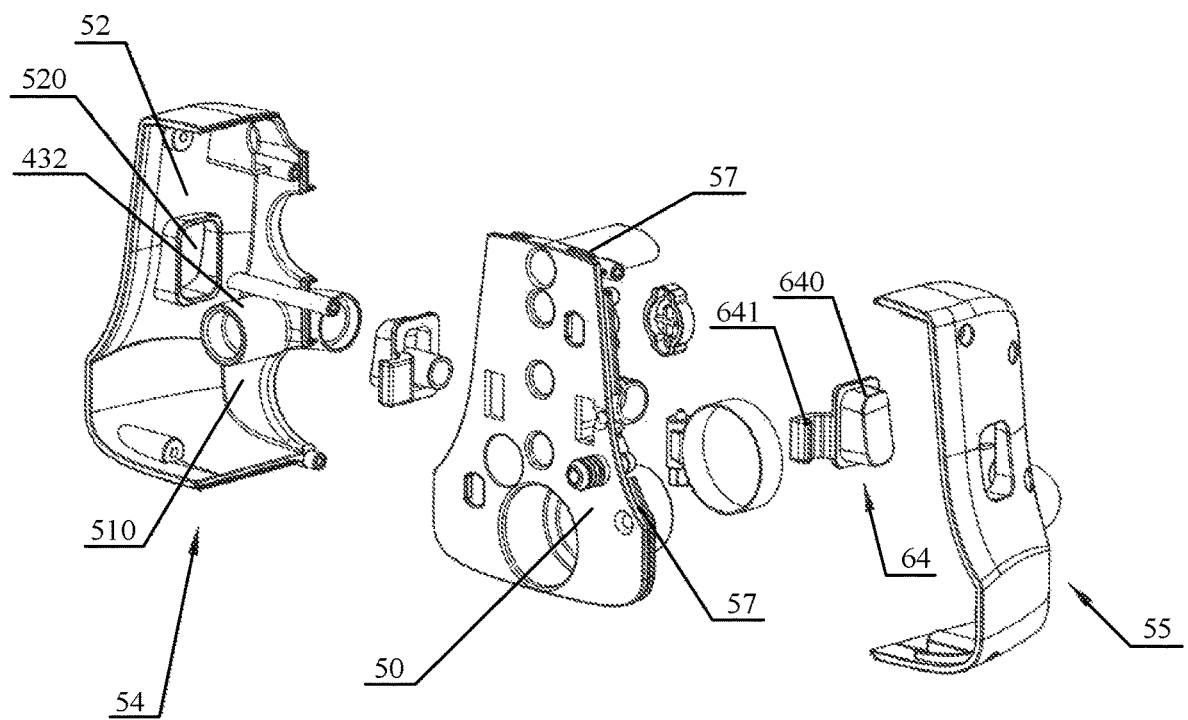
FIG. 11 is an exploded view of a rear part of a wearable working head for a nursing machine viewed from another angle according to an embodiment of the present disclosure.
Figure 12:
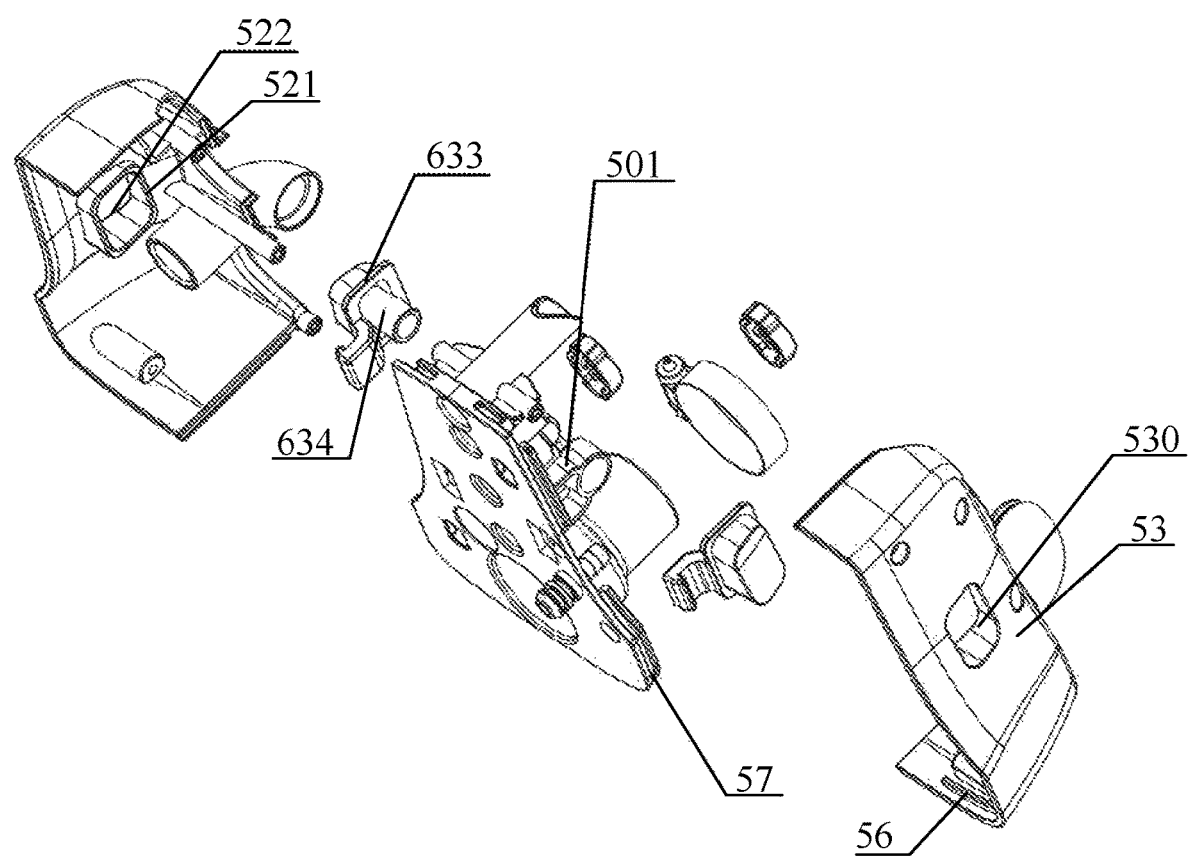
FIG. 12 is an exploded view of a rear part of a wearable working head for a nursing machine viewed from yet another angle according to an embodiment of the present disclosure.
Figure 13:
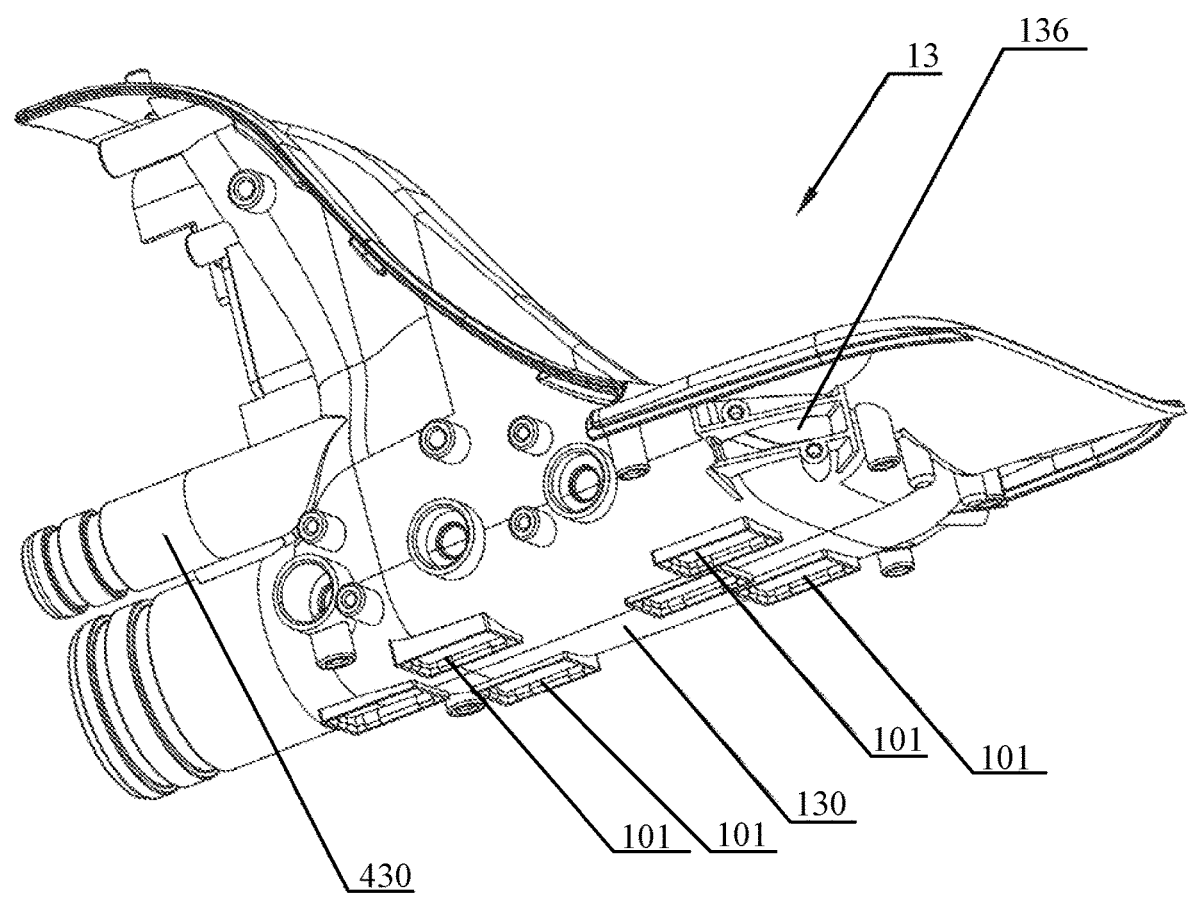
FIG. 13 is a perspective view of a first housing and a first pipe section of a wearable working head for a nursing machine according to an embodiment of the present disclosure.

Referring to FIGS. 11, 12 and 20, the rear part may also be provided with a first through via 520 penetrating the left side wall 52, and a second through via 530 penetrating the right side wall 53. The second locking member 63 may include a first action part 630. The first action part 630 may be operative to move along the first through via 520 toward the fourth locking member 64 under the driving action of the external force thus driving the second locking member 63 to move towards the fourth locking member 64. The fourth locking member 64 may include a second action part 640, which may be operative to move along the second through via 530 toward the second locking member 63 under the driving action of the external force thus driving the fourth locking member 64 to move towards the second locking member 63. The first through via 520 and the second through via 530 each pass through the inside of the rear part and the outside of the rear part, respectively. The first action part 630 includes a first outer plate 631 operative to be directly driven by an external force, a first side plate 632, and a first folded edge 633. An, an outer end of the first side plate 632 is connected to the first outer plate 631. The first folded edge 633 is bent and extends from an inner end of the first side plate 632. The first through via 520 includes a first inner port 521 and first outer port 522 respectively located at an inner end and an outer end of the first through via 520, and the first folded edge 633 blocks on an edge of the first inner port 521 to prevent the first action part 630 from separating outwards from the first through via 520. The first through via 520 and the second through via 530 may further be used for communicating the inner cavity 58 with the outside and improving the ventilation of the inner cavity 58 with the outside.

Each of the first locking member 61 and the third locking member 62 may be a hook. The front side wall 50, the left side wall 52 and the right side wall 53 each surround one side of the inner cavity 58. The front side wall 50 faces the front wearing part. The first locking member 61 and the third locking member 62 each pass backwards through the front side wall 50 to enter the inner cavity 58 of the rear part, and the front side wall 50 is fixedly connected with a first blocking member 500 and a second blocking member 501 arranged in the inner cavity 58. The rear part is further provided with a first restoring spring (not shown in the figures) and a second restoring spring (not shown in the figures). An end of the first restoring spring is blocked by the first blocking member 500, an opposite end is blocked by the second locking member 63, one end of the second restoring spring is blocked by the second blocking member 501, and an opposite end is blocked by the fourth locking member 64. The first blocking member 500 and the second blocking member 501 are spaced apart from each other, or may be directly integrated.

The first blocking member 500 and the second blocking member 501 are each integrally connected to the front side wall 50.

The first blocking member 500 may be provided with a first sleeve 502, the second locking member 63 is provided with a second sleeve 634 nested with the first sleeve 502, a first end of the first restoring spring is received in the first sleeve 502, and the opposite end of the first restoring spring is received in the second sleeve 634. The first restoring spring is in a compressed state. The second sleeve 634 is integrally connected to the first action part 630. The first blocking member 500 and the second blocking member 501 may be symmetrically disposed. An end of the first sleeve 502 may be integrally connected to the first outer plate.

The second locking member 63 may be provided with a first hook 635 locked with the first locking member 61. The first blocking member 500 is provided with a first connecting part 503 integrally connected between the first sleeve 502 and the front side wall 50. The first connecting part 503 and the first locking member 61 are respectively disposed on a left side and a right side of the first hook 635. The first hook 635 is integrally connected to the first folded edge 633. The first connecting part 503 may form a first retreating space 504 configured for receiving the first hook 635. When unlocking, the first hook 635 moves into the first retreating space 504 to unhook and unlock the first locking member 61. The fourth locking member 64 may be provided with a second hook 641 locked with the third locking member 62.

The second sleeve 634 may be internally provided with a positioning protrusion 637, and an end of the first restoring spring is sleeved on the positioning protrusion 637 for positioning.

During assembly, the front wearing part and the rear part are joined together one behind the other, the first locking member 61 is buckled with the second locking member 63, and the third locking member 62 is buckled with the fourth locking member 64. When unlocking, the first action part 630 and the second action part 640 may be simultaneously pushed into the inner cavity 58 by one hand, and the action part 40 may be pushed towards the inside of the inner cavity 21 of the rear part 2, so that the second locking member 4 is pushed into motion, and so the front wearing part and the rear part may be separated, after the first hook 635 is unlocked from the first locking member 61 and the second hook 641 is separated from the third locking member 62. By this design, an unlocking force is balanced in left and right orientation, and deflection during unlocking and docking between the front wearing part and the rear part is reduced.

Figure 21:
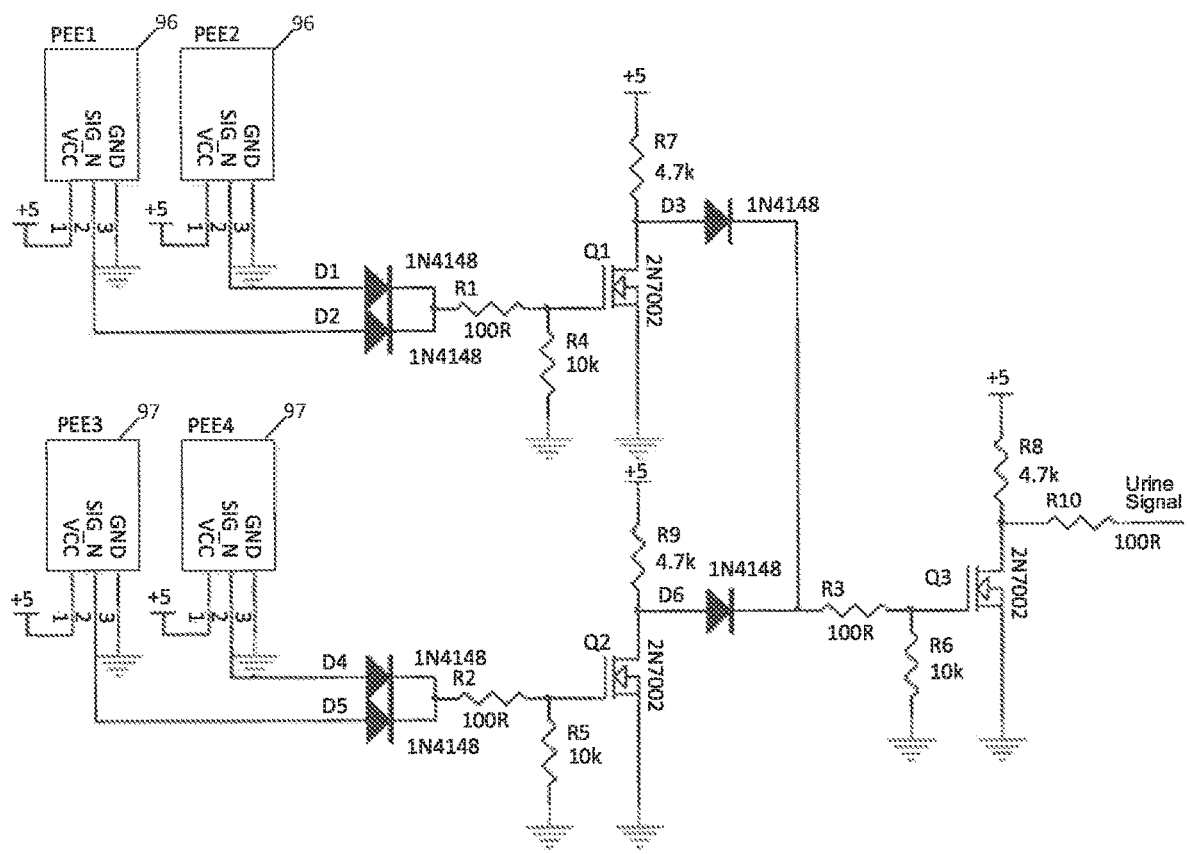
FIG. 21 is a circuit diagram of a urine detection circuit of a wearable working head for a nursing machine according to an embodiment of the present disclosure.

Referring to FIG. 21, the nursing machine may further include a urine detection circuit, which includes a first group of urine sensors and a second group of urine sensors arranged on the working head. The first group of urine sensors includes at least two first urine sensors 96 spaced apart from each other (PEE1 and PEE2 illustrated in FIG. 21 each serve as a first urine sensor 96). The second group of urine sensors includes at least two second urine sensors 97 spaced apart from each other (PEE3 and PEE4 illustrated in FIG. 21 each serve as a second urine sensor 97). When more than one first urine sensor 96 outputs a liquid detected signal or when more than one second urine sensor 97 outputs a liquid detected signal, the urine detection circuit outputs a urine signal; when only one first urine sensor 96 outputs the liquid detected signal or when only one second urine sensor 97 outputs the liquid detected signal or when only one first urine sensor 96 and only one second urine sensor 97 each output the liquid detected signal, the urine detection circuit is configured to not output the urine signal. According to such a design, multiple first urine sensors 96 or multiple second urine sensors 97 need to work cooperatively to finally output the urine signal, which can prevent a small amount of water and other liquid left or condensed in the working head from moving to or staying in a detectable range of one of the urine sensors causing the urine disposing program of the nursing machine to be triggered by mistake, so that an improper start of the urine disposing program, an influence from excessive start of the suction and cleaning operation of the nursing machine, a waste of resources, an influence from frequent cleaning on the patient psychology and normal rest may be avoided. A R5F10369 chip may be arranged inside the working head to receive the urine signal and excreta signal, and it communicates with the main unit to start the cleaning operation. In one embodiment of course, the urine signal and excreta signal may also be directly transmitted to the main unit.

The urine detection circuit may include a first detection circuit, a second detection circuit, and a urine signal circuit, PEE1 and PEE2 belong to the first detection circuit, PEE3 and PEE4 belong to the second detection circuit, and the first detection circuit outputs a high level when both of PEE1 and PEE2 each output a liquid detected signal that a liquid is detected; the first detection circuit outputs a low level when neither of PEE1 and PEE2 outputs the liquid detected signal that a liquid is detected or when only one of them outputs the liquid detected signal that a liquid is detected. The second detection circuit outputs a high level when both of PEE3 and PEE4 each output the liquid detected signal, and the second detection circuit outputs a low level when neither of PEE3 and PEE4 outputs the liquid detected signal or when only one of them outputs the liquid detected signal. Each of PEE1, PEE2, PEE3, and PEE4 may output a low level when a liquid is detected. The first detection circuit may include PEE1, PEE2, a diode D1, a diode D2, a diode D3, a MOS tube Q1, a resistor R1 and a resistor R7, where each of the diode D1, the diode D2 and the diode D3 may have a model of 1N4148, the MOS tube Q1 may have a model of 2N7002, the resistor R1 may have a resistance value of 100R, and the resistor R7 may have a resistance value of 4.7K. The second detection circuit includes PEE3, PEE4, a diode D4, a diode D5, a diode D6, a MOS tube Q2, a resistor R2 and a resistor R7, where each of the diode D4, the diode D5 and the diode D6 may have a model of 1N4148, the MOS tube Q2 may have a model of 2N7002, and the resistor R2 may have a resistance value of 100R. The urine signal circuit includes a MOS tube Q3, a resistor R3, a resistor R8 and a resistor R10, where the MOS tube Q3 may have a model of 2N7002, the resistor R3 may have a resistance value of 100R, the resistor R8 may have a resistance value of 4.7K, and the resistor R10 may have a resistance value of 100R. The urine signal circuit outputs the urine signal (PEE SIGN) through an output terminal. VCC in the each of PEE1, PEE2, PEE5, PEE4 is a power input terminal, which may have a voltage value of positive 5 V, GND is a ground terminal, SIG_N is a signal terminal, the resistor R4 may have a resistance value of 10K, the resistor R5 may have a resistance value of 10K, the resistor R6 may have a resistance value of 10K, and the resistor R9 may have a resistance value of 4.7K. The urine signal circuit may output the urine signal after receiving the high level output by the first detection circuit or the second detection circuit, and the urine signal circuit doesn't output the urine signal after receiving the low level output by the first detection circuit and the second detection circuit. The urine signal output by the urine signal circuit may be a low level, and that the urine signal circuit doesn't output the urine signal may include that the urine signaling circuit outputs a high level. The liquid detected signal output by each of the first urine sensors is a low level, and the liquid detected signal output by each of the second urine sensors is a low level. The first urine sensors 96 and the second urine sensors 97 may be capacitive sensors. In an embodiment, it is necessary for all the first urine sensors 96 each to output the liquid detected signal or all the second urine sensors 97 each to output the liquid detected signal before the urine detection circuit outputs the urine signal. The liquid detected signal output by the first urine sensor 96 may be a low level, and the liquid detected signal output by the second urine sensor 97 may be a low level.

The first group of urine sensors and the second group of urine sensors may be located below the toilet recess 10. The first group of urine sensors are located on a left side of the second group of urine sensors, the first urine sensors 96 are arranged one behind another, and the second urine sensors 97 are arranged one behind another. Multiple mounting slots 101 are provided under the toilet recess 10, the at least two first urine sensors 96 are each arranged in a corresponding one of the multiple mounting slots 101 in one-to-one correspondence, and the at least two second urine sensors 97 are each arranged in a corresponding one of the multiple mounting slots 101 in one-to-one correspondence. Each of the at least two first urine sensors 96 and the at least second urine sensors 97 may be bonded to a corresponding mounting slot 101 by gluing. The mounting slots 101 and the toilet recess 10 may be separately arranged in the first housing 13, and the mounting slots 101 and the toilet recess 10 are arranged back to back. The at least two first urine sensors 96 may be arranged on the bottom surface of the bottom wall 130 and be disposed relatively closer to the left wall 133 than to the right wall 134, and the at least two second urine sensors 97 may be arranged on the bottom surface of the bottom wall 130 and be disposed relatively closer to the right wall 134 than to the left wall 133. The urine sensors may be fixedly adhesive d to the mounting slots 101, and the urine detection circuit may be arranged in the working head.

When more than one first urine sensor 96 outputs a liquid detected signal or when more than one second urine sensor 97 outputs a liquid detected signal, it may be regarded as that a urination is performed by the human body, which will trigger a disposal action of a human excreta, and when only one first urine sensor 96 outputs the liquid detected signal or only one second urine sensor 97 outputs the liquid detected signal or only one first urine sensor 96 and one second urine sensor 97 each output the liquid detected signal, it is regarded as that no urination is performed by the human body, thus the disposal action of the human excreta is not triggered. When more than one first urine sensor 96 outputs the liquid detected signal or when more than one second urine sensor 97 outputs the liquid detected signal, the urine disposing program of the nursing machine is triggered, and when only one first urine sensor 96 outputs the liquid detected signal or only one second urine sensor 97 outputs the liquid detected signal or only one first urine sensor 96 and one second urine sensor 97 each output the liquid detected signal, the urine disposing program of the nursing machine is not triggered.

It may also be designed that when more than one urine sensor outputs the liquid detected signal, the urine detection circuit outputs the urine signal, and when only one urine sensor outputs the liquid detected signal, the urine detection circuit does not output the urine signal. When more than one urine sensor outputs the liquid detected signal, it is considered that a urination session is performed by the human body, and when only one urine sensor outputs the liquid detected signal, it is not considered that no urination session is performed by the human body. In an embodiment, the urine disposing program of the nursing machine is triggered when more than one urine sensor outputs the liquid detected signal, and the urine disposing program of the nursing machine is not triggered when only one urine sensor outputs the liquid detected signal.

What is claimed is:

1. A wearable working head for a nursing machine, comprising a front wearing part, a rear part assembled together with the front wearing part, and an air supplement pipeline, wherein the front wearing part is provided with an air supplement port and a toilet recess; wherein an inner cavity of the rear part is in communication with the outside of the working head; the air supplement pipeline comprises a first end and a second end that are opposite to each other, the air supplement port forms a first end port of the air supplement pipeline, and a second end port of the air supplement pipeline is in a direct communication with the inner cavity of the rear part; and air in the inner cavity of the rear part is allowed to enter the air supplement pipeline via the second end port and further be supplied to the toilet recess via the air supplement port.

2. The wearable working head as recited in claim 1, wherein the air supplement pipeline further comprises an outer bending section disposed outside the rear part, and wherein two opposite ends of the outer bending section are each connected to the rear part.

3. The wearable working head as recited in claim 2, wherein the outer bending section comprises a left bending section and a right bending section that are joined together.

4. The wearable working head as recited in claim 3, wherein the rear part comprises a front side wall and a rear end wall that are opposite to each other in front and back orientation, a left side wall and a right side wall that are opposite to each other in left and right orientation; the front side wall, the rear end wall, the left side wall, and the right side wall surround the inner cavity; the front side wall faces the front wearing part, and the rear end wall comprises a rear end wall left part and a rear end wall right part; the left bending section is connected to the rear end wall left part, and the right bending section is connected to the rear end wall right part, the rear end wall left part and the rear end wall right part are joined together in left and right orientation, and the left bending section and the right bending section are joined together in left and right orientation; wherein the second end port is opened at the rear end wall right part and forms an end port of the right bending section.

5. The wearable working head as recited in claim 4, wherein the front wearing part comprises a first housing and the toilet recess is defined in the first housing, the air supplement pipeline comprises a first pipe section integrally connected to the first housing, a second pipe section integrally connected to the front side wall, and a third pipe section integrally connected to the left bending section; wherein the first pipe section is joined with the second pipe section, the second pipe section is joined with the third pipe section, the second pipe section and the third pipe section are disposed in the inner cavity of the rear part, and the first pipe section passes backwards through the front side wall to enter the inner cavity of the rear part.

6. The wearable working head as recited in claim 5, wherein the front wearing part further comprises a tray configured to directly or indirectly support buttocks of the human body, wherein the toilet recess is defined in the tray and is configured to receive an excreta; the tray is provided with a front edge portion disposed in front of the toilet recess, the front edge portion defining a concave area corresponding to a tailbone of the human body.

7. The wearable working head as recited in claim 6, wherein the front edge portion is a part of the first housing, the first housing comprising a bottom wall and a front wall extending upward from a front edge of the bottom wall, wherein the front wall is integrally connected to the front edge portion and blocks on a rear side of the concave area.

8. The wearable working head as recited in claim 7, wherein a recess between the concave area and the toilet recess is defined above the front wall, the concave area is covered with a cushion, and the cushion covers the recess.

9. The wearable working head as recited in claim 8, wherein the part of the cushion covering the concave area is thicker than the part of the cushion covering the recess.

10. The wearable working head as recited in claim 9, wherein
the tray is further provided with a left front nozzle and a right front nozzle configured for spraying water towards an inside of the toilet recess, wherein the left front nozzle is disposed at a left rear side of the concave area, and the right front nozzle is disposed at a right rear side of the concave area.

11. The wearable working head as recited in claim 10, wherein the tray is further provided with a first water inlet connector, a first connection water pipe having two ends, a second connection water pipe having two ends, and a third connection pipe having three ends; wherein the first connection water pipe connects a first end of the third connection pipe to the left front nozzle, the second connection water pipe connects a second end of the third connection pipe to the right front nozzle, and a third end of the third connection water pipe is connected to the first water inlet connector.

12. The wearable working head as recited in claim 11, wherein the left front nozzle and the right front nozzle are each fixed to the first housing, the first housing comprises a left front mounting through slot disposed on a left front side of the toilet recess and a right front mounting through slot disposed on a right front side of the toilet recess, wherein the left front nozzle is mounted in the left front mounting through slot, and the right front nozzle is mounted in the right front mounting through slot.

13. The wearable working head as recited in claim 12, wherein each of the left front nozzle and the right front nozzle comprises a first nozzle part and a second nozzle part, the first nozzle part is integrally provided with a second water inlet connector, the first nozzle part and the second nozzle part enclose a nozzle water cavity configured such as to allow water to be sprayed out via a water outlet defined in the first nozzle part after entering the nozzle water cavity via the second water inlet connector.

14. The wearable working head as recited in claim 13, further comprising a locking structure configured for locking the front wearing part to the rear part; the locking structure comprises a first locking member arranged on the front wearing part, a second locking member arranged on the rear part, a third locking member arranged on the front wearing part, and a fourth locking member arranged on the rear part; the first locking member and the second locking member are locked together, and the third locking member and the fourth locking member are locked together; the second locking member is operative to move towards the fourth locking member under the action of an external force to be unlocked with the first locking member, and the fourth locking member is operative to move towards the second locking member under an external force to be unlocked with the third locking member.

15. The wearable working head as recited in claim 14, wherein the rear part is further arranged with a left side wall, a right side wall opposite to the left side wall, a first through via penetrating the left side wall, and a second through via penetrating the right side wall; the second locking member comprises a first action part operative to move along the first through via toward the fourth locking member under the driving action of the external force thus driving the second locking member to move towards the fourth locking member, and the fourth locking member comprises a second action part operative to move along the second through via toward the second locking member under the driving action of the external force thus driving the fourth locking member to move towards the second locking member.

16. The wearable working head as recited in claim 15, wherein the first action part comprises a first outer plate operative to be directly driven by an external force, a first side plate, and a first folded edge; an outer end of the first side plate is connected to the first outer plate; the first folded edge is bent and extends from an inner end of the first side plate; the first through via comprises a first inner port and first outer port respectively located at an inner end and an outer end of the first through via, and the first folded edge blocks at an edge of the first inner port.

17. The wearable working head as recited in claim 16, wherein the rear part is provided with an inner cavity, a front side wall, and a left side wall and a right side wall that are opposite to each other; the front side wall, the left side wall, and the right side wall each surround at a side of the inner cavity, and the front side wall faces the front wearing part, and the first locking member passes backwards through the front side wall to enter the inner cavity of the rear part; the front side wall is fixedly connected with a first blocking member disposed in the inner cavity; the rear part is further provided with a first restoring spring, wherein a first end of the first restoring spring is blocked by the first blocking member and a second end of the first restoring spring opposite to the first end is blocked by the second locking member.

18. The wearable working head as recited in claim 17, wherein the first blocking member is provided with a first sleeve, the second locking member is provided with a second sleeve nested with the first sleeve, and wherein the first end of the first restoring spring is received in the first sleeve, and the second end of the first restoring spring is received in the second sleeve.

19. The wearable working head as recited in claim 18, wherein the second locking member is provided with a first hook locked with the first locking member, the first blocking member is provided with a first connecting part integrally connected between the first sleeve and the front side wall, and the first connecting part and the first locking member are respectively disposed on a left side and a right side of the first hook.

20. The wearable working head as recited in claim 19, wherein the first connecting part defines a first retreating space configured for receiving the first hook.

* * * * *